(12) United States Patent
Volckens et al.

(10) Patent No.: US 9,618,439 B2
(45) Date of Patent: Apr. 11, 2017

(54) THERMOPHORETIC SAMPLER

(71) Applicants: Colorado State University Research Foundation, Fort Collins, CO (US); RJ Lee Group, Monroeville, PA (US)

(72) Inventors: John Volckens, Fort Collins, CO (US); Gary Casuccio, Brave, PA (US); Henry P. Lentz, Apache Junction, AZ (US); Anthony Marchese, Fort Collins, CO (US); John T. Mastovich, Murrysville, PA (US); Daniel David Miller-Lionberg, Fort Collins, CO (US); Judith Chun-Hsu Yang, Pittsburgh, PA (US)

(73) Assignees: Colorado State University Research Foundation, Fort Collins, CO (US); RJ Lee Group, Inc., Monroeville, PA (US)

( * ) Notice: Subject to any disclaimer, the term of this patent is extended or adjusted under 35 U.S.C. 154(b) by 81 days.

(21) Appl. No.: 14/614,192

(22) Filed: Feb. 4, 2015

(65) Prior Publication Data

US 2015/0143929 A1    May 28, 2015

Related U.S. Application Data

(63) Continuation-in-part of application No. 13/480,322, filed on May 24, 2012, now Pat. No. 8,973,447.

(60) Provisional application No. 61/489,598, filed on May 24, 2011.

(51) Int. Cl.
G01N 15/06 (2006.01)
G01N 1/22 (2006.01)
G01N 15/00 (2006.01)

(52) U.S. Cl.
CPC ....... *G01N 15/0606* (2013.01); *G01N 1/2202* (2013.01); *G01N 1/2208* (2013.01); *G01N 1/2247* (2013.01); *G01N 1/2273* (2013.01); G01N 2001/2276 (2013.01); G01N 2015/0038 (2013.01)

(58) Field of Classification Search
CPC .............. G01N 1/2205; G01N 1/2208; G01N 2001/2223; G01N 2001/2276; G01N 1/2273; G01N 2015/0046
See application file for complete search history.

(56) References Cited

U.S. PATENT DOCUMENTS

| | | | |
|---|---|---|---|
| 6,666,905 B2 | 12/2003 | Page et al. | |
| 2002/0014158 A1* | 2/2002 | Page | B01D 21/0009 95/289 |
| 2012/0175289 A1 | 7/2012 | Bystron et al. | |

OTHER PUBLICATIONS

Azong-Wara et al. "Optimisation of a thermophoretic personal sampler for nanoparticle exposure studies". J Nanopart Res. vol. 11. pp. 1611-1624. 2009.

Gonzalez et al. "A New Thermophoretic Precipitator for Collection of Nanometer-Sized Aerosol Particles". Aerosol Science and Technology. vol. 39. pp. 1064-1071. 2005.

(Continued)

*Primary Examiner* — Paul West
(74) *Attorney, Agent, or Firm* — Faegre Baker Daniels LLP

(57) ABSTRACT

A thermophoretic sampler includes a sample assembly into which a removable sample cartridge can be inserted. The sample cartridge holds a substrate that, upon insertion, is exposed to a sample chamber. Thermophoresis is induced in the sample chamber, causing nanoparticles to be deposited on the substrate.

20 Claims, 13 Drawing Sheets

(56) References Cited

OTHER PUBLICATIONS

Lorenzo et al. "A Thermophoretic Precipitator for the Representative Collection of Atmospheric Ultrafine Particles for Microscopic Analysis". Aerosol Science and Technology. vol. 41: Issue 10. pp. 934-943. 2007.
Miller et al. A Handheld Electrostatic Precipitator for Sampling Airborne Particles and Nanoparticles. Aerosol Science and Technology. vol. 44: Issue 6. pp. 417-427. Apr. 20, 2010.
Miller et al. "Design Optimization of a Portable Thermophoretic Precipitator Nanoparticle Sampler". Aerosol Science and Technology. vol. 46: Issue 8. pp. 897-904. 2012.
Peters et al. "Impactors, Cyclones, and Other Particle Collectors". American Conference of Governmental Industrial Hygienists (ACGIH). pp. 1-39. 2008.

\* cited by examiner

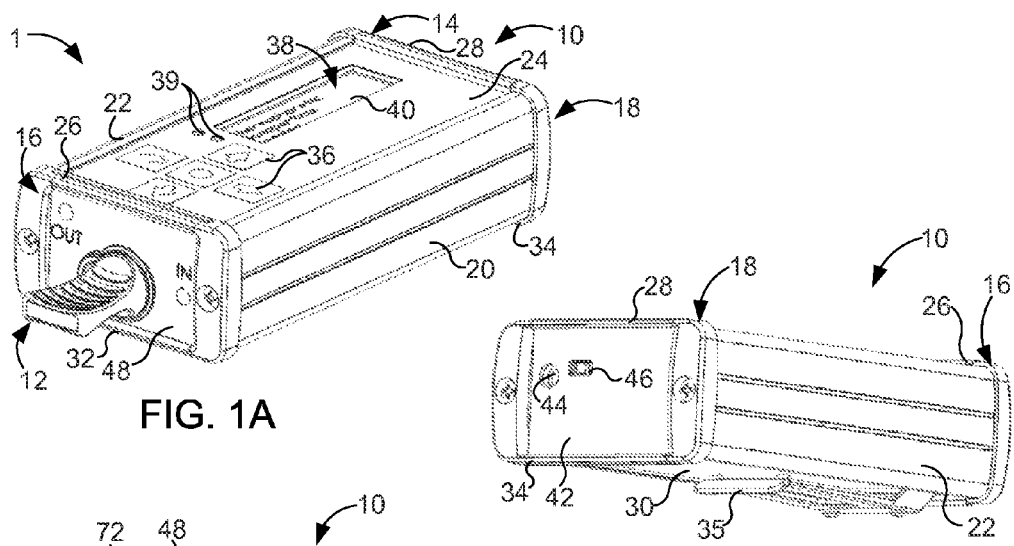
FIG. 1A
FIG. 1B
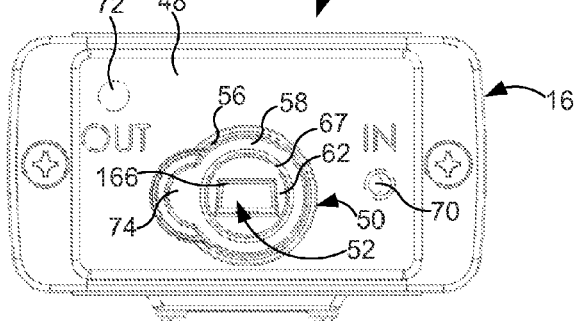
FIG. 1C
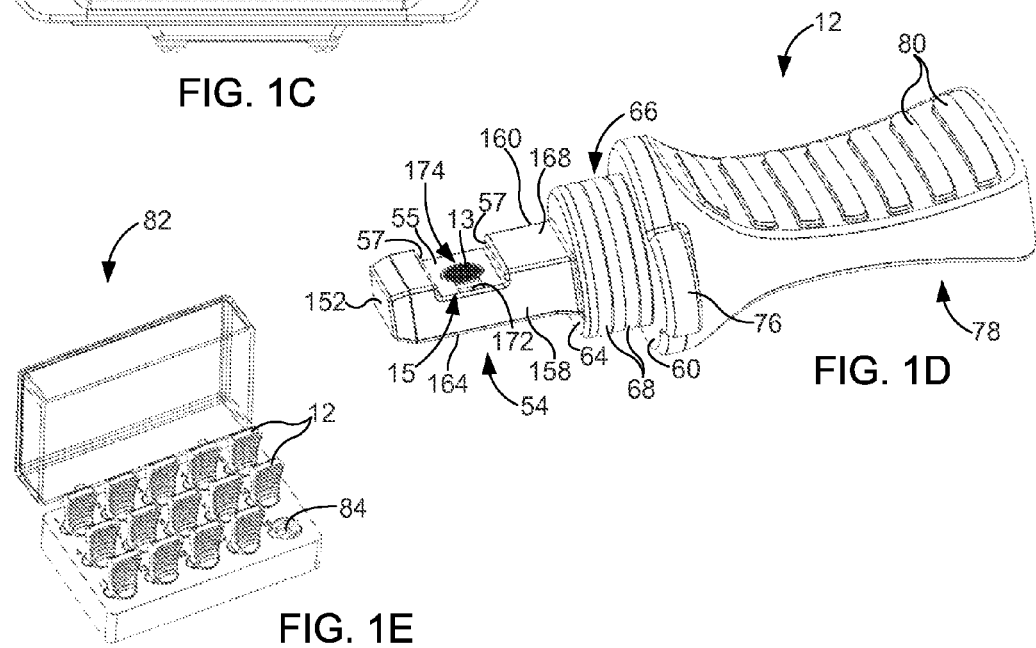
FIG. 1D
FIG. 1E

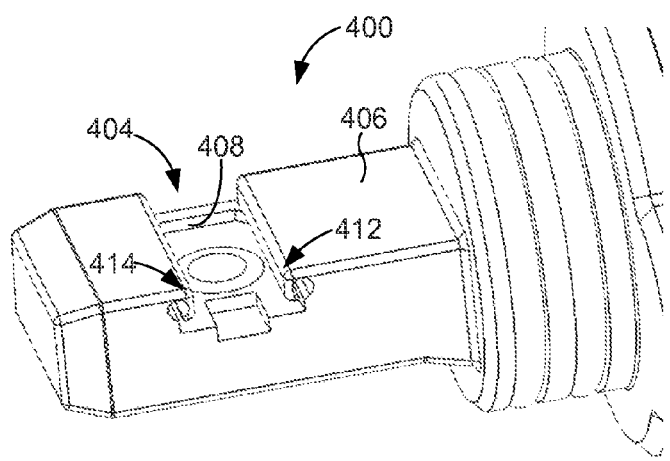
FIG. 4A
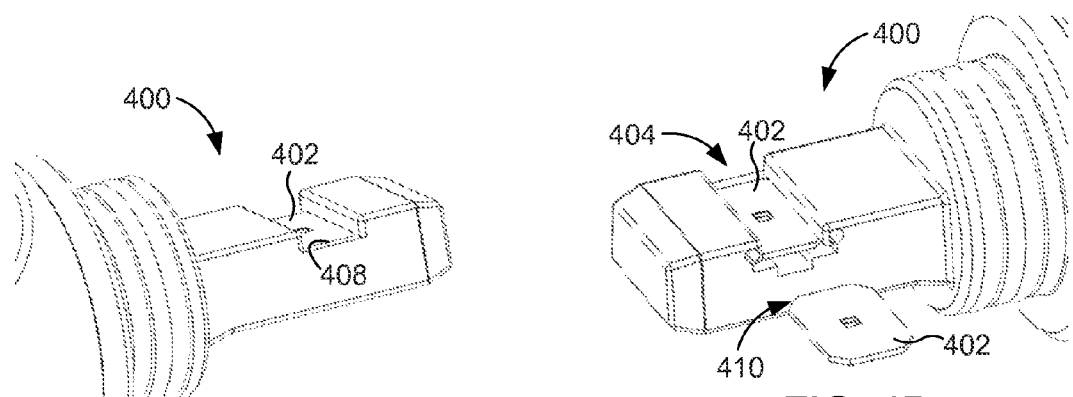
FIG. 4C
FIG. 4B
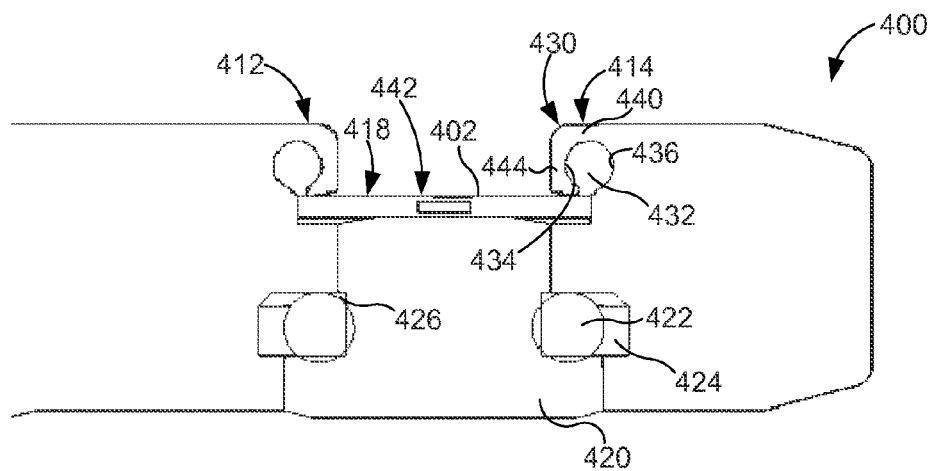
FIG. 4D

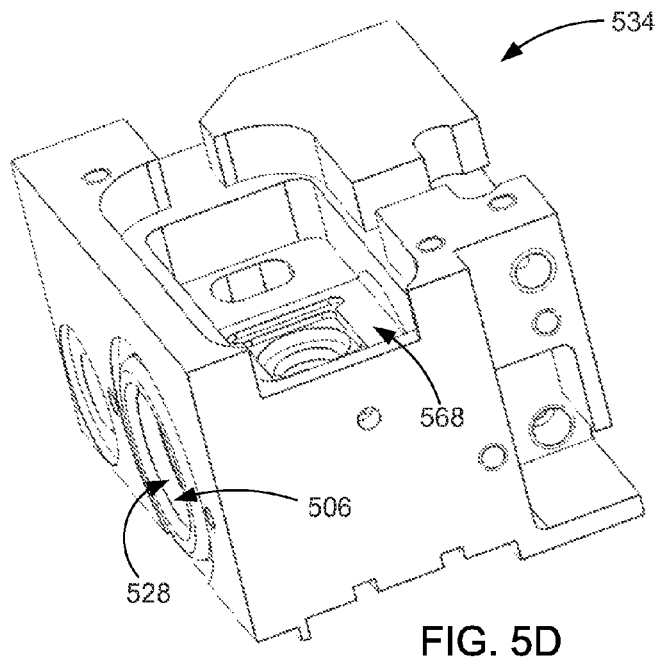
FIG. 5D
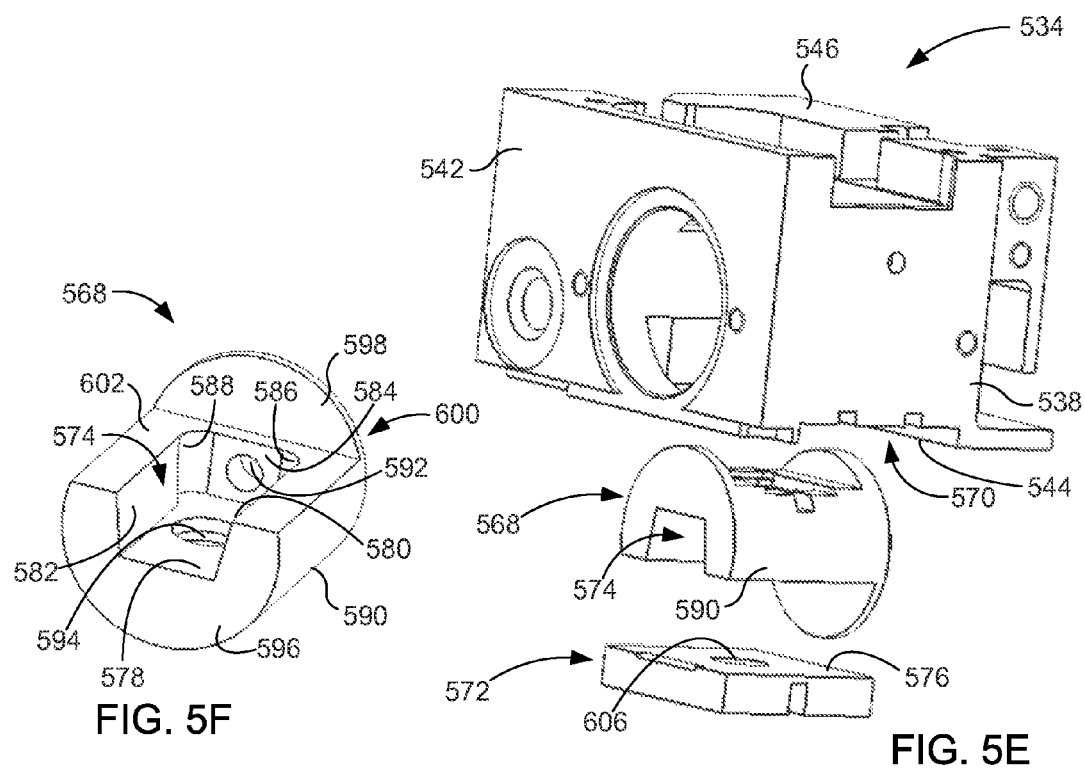
FIG. 5F
FIG. 5E

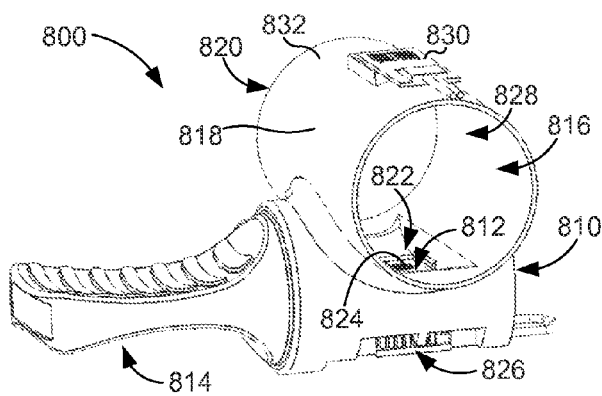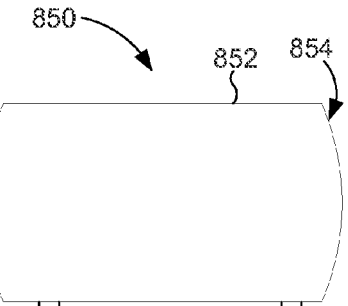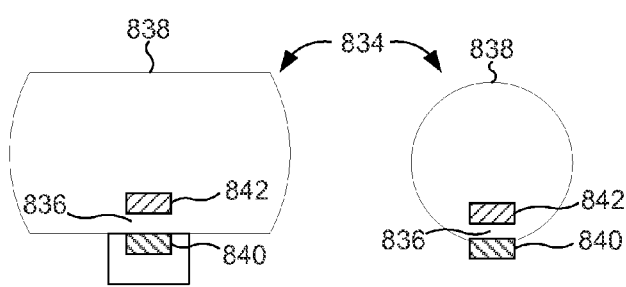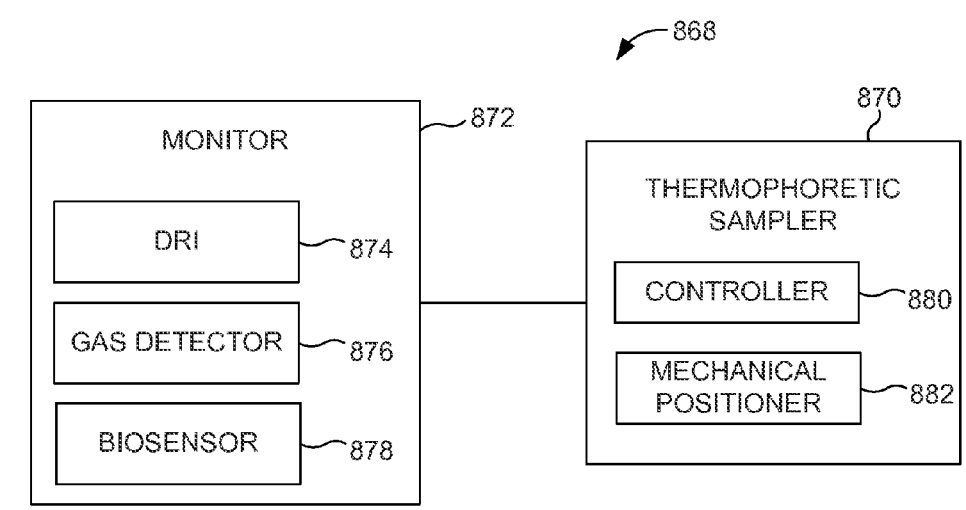
FIG. 8A
FIG. 8B
FIG. 8C
FIG. 8D
FIG. 8E

THERMOPHORETIC SAMPLER

CROSS-REFERENCE TO RELATED APPLICATIONS

This application is a continuation-in-part of U.S. application Ser. No. 13/480,322, filed May 24, 2012, entitled "Thermophoretic Sampler," which claims priority to U.S. Provisional Application No. 61/489,598, filed May 24, 2011, entitled "Personal, Thermophoretic Sampler for Airborne Nanoparticles," each of which is hereby incorporated by reference in its entirety for all purposes.

STATEMENT REGARDING FEDERALLY SPONSORED RESEARCH OR DEVELOPMENT

The subject matter of this disclosure was made with government support under Grant No. R03 OH009381 awarded by the Centers for Disease Control. The government has certain rights in the subject matter.

BACKGROUND

Advances in the nanotechnology industry and related economic rewards are being questioned from the perspective of potential health effects associated with exposure to nanomaterials. Some suspect the slowing of the financial investment in nanotechnology may be related to the potential health risks. Higher quality health risk assessments can be facilitated by capturing engineered nanoparticles and differentiating them from naturally occurring counterparts.

As the nanotechnology industry expands, there is growing concern among scientists, policymakers, and consumers regarding the health and safety impacts that nanomaterial proliferation may exert on humans and the environment. For example, if a certain nanomaterial exhibits altered physiochemical behavior, it may also exert unknown and unpredicted effects within the environment or the human body. While the debate regarding such effects has yet to be resolved scientifically, there is some evidence supporting the increased toxicity of nanoscale materials. Additional concerns with nanoparticles include their ability to cross tissue barriers and translocate to different areas of the body. For example, inhaled nanoparticles have been shown to undergo extra-pulmonary translocation into the systemic circulation, with subsequent deposition in peripheral tissues.

Methods for nanoparticle speciation are useful because biogenic (e.g., sea salt) and anthropogenic (e.g., diesel soot) nanoparticles often outnumber airborne concentrations of engineered nanoparticles, even in locations where engineered nanoparticles are being produced and handled. Consequently, an exposure assessment that distinguishes engineered nanomaterials from biogenic and incidental nanoparticles can be useful, especially if the goal is to investigate environmental health and safety impacts resulting from exposure. Current nanoparticle measurement methods using only direct reading instruments (DRI) typically do not include nanoparticle identification.

SUMMARY

Embodiments of the disclosed subject matter include a miniaturized thermophoretic sampler. Embodiments of the thermophoretic sampler permit collection of nanoparticles that can be speciated using analytical techniques. Embodiments of the sampler can collect nanoparticles from a person's breathing zone to facilitate worker exposure and risk assessment studies.

In embodiments, a thermophoretic sampling device includes a sample chamber housing, comprising a sample chamber defined within the sample chamber housing, the sample chamber defining a portion of a flow path for air; and a cartridge channel defined within the sample chamber housing. The device may also include a sample cartridge configured to be removably inserted into the cartridge channel. In embodiments, the sample cartridge includes a substrate, coupled to first portion of the sample cartridge, the substrate having a collection surface configured to be exposed to a first region of the sample chamber in response to the sample cartridge being inserted into the cartridge channel; an air inlet defined in a first end of a second portion of the sample cartridge; and an inlet duct extending from the air inlet to an aperture defined in a second end of the second portion of the sample cartridge, wherein the inlet duct is configured to allow air to move from the air inlet to the sample chamber.

Embodiments include a system for collecting nanoparticles on a substrate. The system may include a sample core assembly having a sample chamber defined therein, and the sample core assembly may include an opening defined in an outside wall of the sample core assembly; a cooling mechanism; and a cartridge channel extending from the opening to the sample chamber. The system may also include a sample cartridge configured to be removably inserted into the cartridge channel through the opening. According to embodiments, the sample cartridge may include a first portion configured to be disposed within the cartridge channel; a second portion adjacent to the first portion; an air inlet disposed in a first end of the second portion; and an inlet duct disposed within the second portion, the inlet duct extending from the air inlet to an aperture defined in a second end of the second portion. The system may also include a substrate removably coupled to the sample cartridge, where the cooling mechanism is configured to be thermally coupled to the substrate in response to the sample cartridge being inserted into the cartridge channel.

Embodiments may also include a method for collecting nanoparticles on a substrate. According to embodiments, the method may include receiving a sample cartridge, having a substrate removably coupled thereto, within a sample core assembly. The sample core assembly may include a cartridge channel configured to receive a first portion of the sample cartridge, where the sample core assembly includes a sample chamber defining a portion of a flow path for air, and where the sample cartridge comprises an air inlet defined in a first end and an inlet duct extending from the air inlet to the sample chamber. Embodiments of the method may also include maintaining the substrate at a temperature that is lower than a temperature of a warm region of the sample chamber such that thermophoresis causes nanoparticles to be deposited on the substrate.

While multiple embodiments are disclosed, still other embodiments of the subject matter will become apparent to those skilled in the art from the following detailed description, which shows and describes illustrative embodiments of the subject matter. Accordingly, the drawings and detailed description are to be regarded as illustrative in nature and not restrictive.

BRIEF DESCRIPTION OF THE DRAWINGS

FIGS. 1A and 1B are perspective views of a thermophoretic sampler in accordance with embodiments of the disclosure;

FIG. 1C is a front view of the thermophoretic sampler of FIGS. 1A and 1B accordance with embodiments of the disclosure;

FIG. 1D is a perspective view of a sample cartridge in accordance with embodiments of the disclosure;

FIG. 1E is a perspective view of a sample cartridge carrying case in accordance with embodiments of the disclosure;

FIGS. 4A-4C are perspective views of a sample cartridge in accordance with embodiments of the disclosure;

FIG. 4D is a cross-sectional side view of a sample cartridge in accordance with embodiments of the disclosure;

FIG. 5D is a perspective view of a sample chamber housing in accordance with embodiments of the disclosure;

FIG. 5E is an exploded perspective view of the sample chamber housing of FIG. 5D in accordance with embodiments of the disclosure;

FIG. 5F is an inverted perspective view of a sample core insert in accordance with embodiments of the disclosure;

FIG. 8A is a perspective view of a thermophoretic sampler in accordance with embodiments of the disclosure;

FIGS. 8B-8D are schematic diagrams depicting thermophoretic samplers in accordance with embodiments of the disclosure;

FIG. 8E is a schematic diagram depicting a thermophoretic sampler coupled to an active monitor in accordance with embodiments of the disclosure;

Figure 1F:
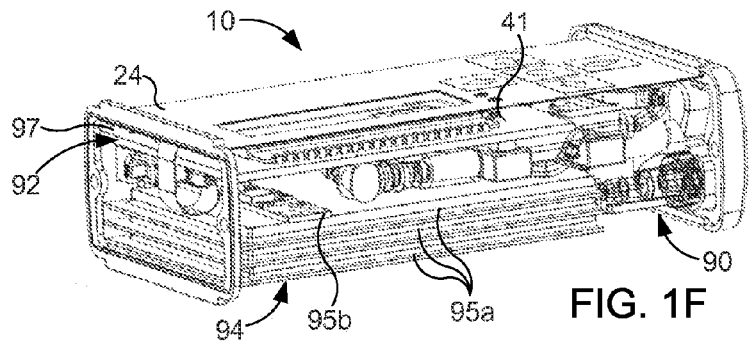
FIG. 1F is an internal perspective view of the thermophoretic sampler of FIGS. 1A and 1B in accordance with embodiments of the disclosure.

While embodiments of the disclosed subject matter are amenable to various modifications and alternative forms, specific embodiments have been shown by way of example in the drawings and are described in detail below. The intention, however, is not to limit the subject matter to the particular embodiments described. On the contrary, the subject matter is intended to cover all modifications, equivalents, and alternatives falling within the ambit of the disclosure as defined by the appended claims.

Moreover, although the term "block" may be used herein to connote different elements of methods or algorithms employed, the term should not be interpreted as implying any particular order among or between various steps herein disclosed unless and except when the order of individual steps is explicitly described.

DETAILED DESCRIPTION

Embodiments of the thermophoretic sampler collect airborne particles by applying a temperature gradient to a sample chamber that defines a portion of an air flow. Because of the temperature gradient (e.g., ~100° C./mm from the top to the bottom of the sample chamber), gas molecules on one side of a particle have greater kinetic energy than those on the opposite side. Molecules on the hotter side transfer more net momentum per collision to the particle, resulting in a thermophoretic force. The movement of a particle in the direction of decreasing temperature, called its thermophoretic velocity, will eventually cause the particle to deposit onto a substrate.

In embodiments, a miniaturized thermophoretic sampler provides the capability of capturing airborne nanoparticles via thermophoretic force directly onto a transmission electron microscope (TEM) substrate. In embodiments, different types of substrates can be used to enable capture and subsequent analyses of nanoparticles in various analytical instruments and related techniques such as, for example, excitation tools including electron-ion (e.g., SEM, EMPA, etc.), x-ray (e.g., XPS, XRF, XRD, etc.), laser/light (e.g., Raman, LICP, FTIR, PLM, etc.), and/or the like. Additionally, embodiments include combining a thermophoretic sampler with other nanoparticle measurement devices such as, for example, direct reading instruments (DRIs), biosensors, gas detectors, nanoparticle sizers, particle counters, and/or the like.

FIGS. 1A-1H depict an illustrative personal thermophoretic sampler 1. In embodiments, the sampler 1 can be worn or carried by a user to facilitate collection of nanoparticles from the user's environment such as, for example, in a region corresponding to air that the user breaths. The sampler 1 includes a sampler assembly 10 and a removable sample cartridge 12 to which a substrate 13 can be removably coupled. According to embodiments, when the cartridge 12 is inserted in the sampler assembly 10, the substrate 13 is exposed to a sample chamber 117 (illustrated in FIGS. 2A and 2B) and thermophoresis causes nanoparticles to be deposited on the substrate 13. According to embodiments, the substrate 13 can be a transmission electron microscopy grid, a thin foil substrate, any number of other types of substrates, and/or the like. As shown in FIGS. 1A and 1B, the sampler assembly 10 includes a housing 14 having a front frame 16, a rear frame 18 and a pair of opposed side walls 20 and 22, extending between the front and rear frames 16 and 18. A top plate 24 extends between a top edge 26 of the front frame 16 and a top edge 28 of the rear frame 18 and a bottom plate 30 extends between a bottom edge 32 of the front frame 16 and a bottom edge 34 of the rear frame 18. As shown in FIG. 1, the housing 14 has a generally rectangular shape, although in embodiments, any number of other configurations can be used for the housing 14. In embodiments, as illustrated, the housing 14 can include a clip 35 that is coupled, for example, to the bottom plate 30 and that can be used to clip the sampler 1 to an article of clothing. In embodiments, the housing 14 can include other mechanisms for facilitating wearing of the sampler 1 by a user such as, for example, a strap, a hook-and-loop system (e.g., Velcro®), and/or the like.

In embodiments, the top plate 24 and/or any number of other surfaces of the housing 14, can include any number of input devices 36 such as, for example, buttons, a touchscreen, switches, roller, slider, and/or the like. In the illustrated embodiments, the top plate 24 includes an aperture 38 that serves as a window through which a display 40 device can be viewed. In embodiments, the display device 40 can be, for example, an LCD screen, an LED screen, one or more LED lights, a touch-screen, and/or the like. As shown, the top plate 24 includes apertures 39 through which LED indicator lights 41 can be viewed. In embodiments, for example, the LED indicator lights 41 can be used to indicate whether the sampler 1 is powered on or off.

As shown in FIG. 1B, the housing 14 includes a rear plate 42 held in place by the rear frame 18. The rear plate 42 includes an aperture 44 for receiving a charging plug (not shown) and a switch 46 for powering up the sampler 1. In embodiments, other input/output jacks, switches, and/or the like can be included on the rear plate 42 (and/or, in embodiments, on other surfaces defining the housing 14).

As shown in FIGS. 1A and 1C, the housing 14 includes a front plate 48 held in place by the front frame 16. In the illustrated embodiments, the front plate 48 includes a cartridge port 50 for receiving the sample cartridge 12. As shown, a cartridge channel 52 extends from the cartridge port 50 into the sampler assembly 10 and is configured for receiving a first portion 54 of the sample cartridge 12, which includes the substrate 13. In the illustrated embodiments, the cartridge channel 52 has a generally trapezoidal shape, which corresponds to a generally trapezoidal shape of the first portion 54 of the sample cartridge. According to embodiments, using a shape that is asymmetrical with respect to at least one plane can facilitate proper insertion of the cartridge 12. For instance, in the illustrated embodiments, the trapezoidal shape of the cartridge 12 and the corresponding cartridge channel 52 can prevent a user from inserting the cartridge 12 upside-down, in which case substrate 13 would not be exposed to the sample chamber. In other embodiments, the cartridge channel 52 and the first portion 54 of the cartridge can be configured according to other shapes, depending on the details of the implementation, such as, for example, rectangular shapes, circular shapes, triangular shapes, pentagonal shapes, and/or the like.

As shown, the cartridge port 50 includes a first surface 56 extending from the front plate 48 to a first stopping surface 58, which may lie in a plane substantially parallel to the front plate 48. According to embodiments, when the sample cartridge 12 is fully inserted through the cartridge port 50, the first stopping surface 58 engages a surface 60 on the sample cartridge 12 and a second stopping surface 62, defined within the cartridge port 50, engages a second surface 64 on the sample cartridge. In this fully inserted position, a sealing portion 66 of the sample cartridge 12 engages a second surface 67 of the cartridge port 50 to create a seal from the outside environment. In embodiments, as shown in FIG. 1D, the sealing portion 66 of the sample cartridge 12 includes one or more sealing mechanisms 68 such as, for example, o-rings, gaskets, and/or the like. In embodiments, the second surface 67 can be ribbed or otherwise contoured to facilitate the sealing action of the sealing mechanisms 68. When the sample cartridge 12 is fully inserted, thereby causing the cartridge port 50 to be sealed from the outside environment, air enters and exits the sampler assembly 10 through an air inlet 70 and an air outlet 72, respectively. In embodiments, as shown in FIG. 1C, the air inlet 70 and outlet 72 can be defined in the front plate 48, while, in other embodiments, the air inlet 70 and air outlet 72 can be defined in other surfaces of the housing 14.

In embodiments, as shown in FIGS. 1C and 1D, the cartridge port 50 can include a guide feature 74 that corresponds to a protrusion 76 on the sample cartridge 12 to facilitate proper orientation when inserting the sample cartridge 12. Additionally, the sample cartridge 12 can include a handle portion 78 that can be gripped by a user for facilitating insertion and removal of the sample cartridge. In embodiments, the handle portion 78 can include any number of various types of grip features 80 to facilitate gripping by a user. In embodiments, the handle portion 78 may include low thermal conductivity plastic, whereas the first portion 54 may include high thermal-conductivity materials, which may maximize heat flow to the sample chamber (not shown) while minimizing heat flow to the surrounding enclosure. Additionally, in embodiments, the sampler 1 may be accompanied by a carrying case 82 that can be used to carry a number of sample cartridges 12. In embodiments, a number of different samples may be collected using different cartridges 12, which can be stored in the case 82 and transported to a destination for analysis. According to embodiments, the case 82 can include any number of slots 84 for holding cartridges and can be configured according to any number of different designs. In embodiments, the case 82 is configured to be sealed when it is closed, thereby facilitating avoiding exposure of the sample cartridges to contamination.

Figure 1G:
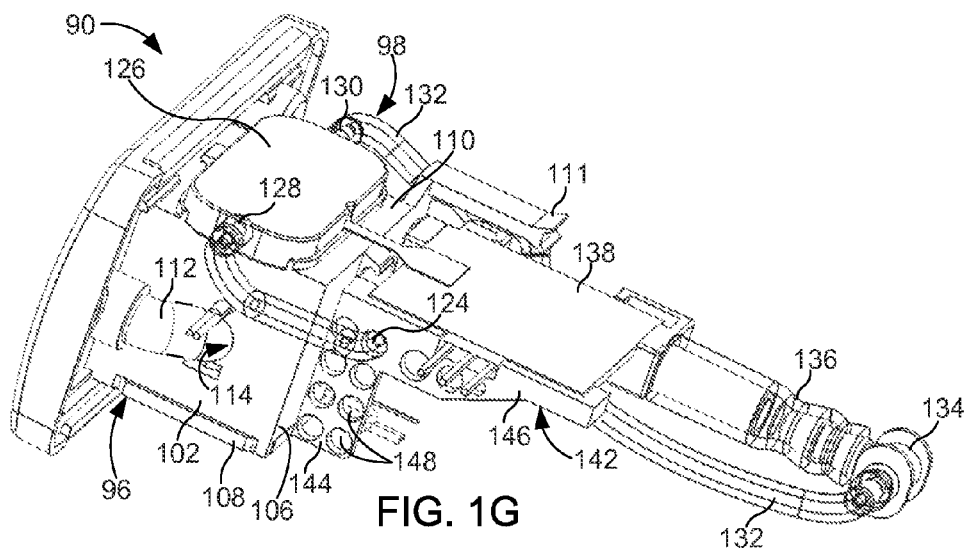
FIGS. 1G and 1H are perspective views of a sample core assembly in accordance with embodiments of the disclosure.

FIGS. 1F and 1G show internal views of the illustrative sampler assembly 10. As shown, the sampler assembly 10 includes a sample core assembly 90, a controller 92, and a battery assembly 94. According to embodiments, the controller 92 can include a microcontroller, a central processing unit (CPU), a programmable logic device (PLD), software, hardware, firmware, or any combination these and/or other components. The controller 92, as well as other electrical components of the sampler assembly 10, is powered by the battery assembly 94. In embodiments, the battery assembly 94 can include rechargeable battery cells 95*a*, a battery cell protection circuit 95*b*, and/or the like. The battery cells 95*a* can include, for example, lithium ion battery cells. In embodiments, the components 90, 92, and 94 can be configured within the housing 14 in any number of different arrangements.

Figure 1H:
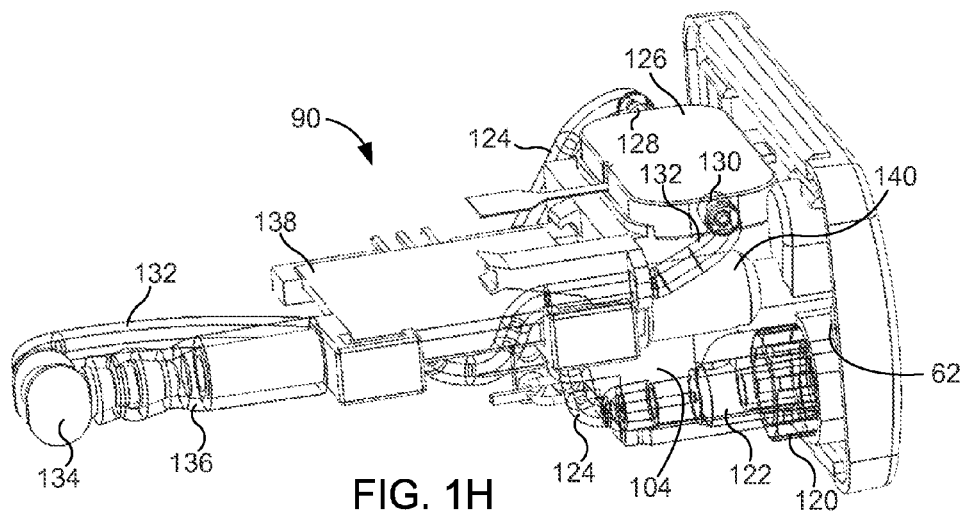

As depicted in FIG. 1G, the sample core assembly 90 includes a sample chamber housing 96 and an air flow assembly 98. The sample chamber housing 96 includes side walls 102 and 104, a rear wall 106, a front wall 62 (as shown in FIG. 1C), a lower wall 108, and an upper wall 110. Additionally, as shown in FIGS. 1F-1H, a stopping arm 111 can be mounted to the sample core assembly 90 for holding in place a printed circuit board (PCB) 97, which is a component of the controller 92.

The air flow assembly 98 provides a portion of an air flow path through the sampler assembly 10. According to embodiments, any number of different types of air flow assemblies can be used to facilitate moving air through the sample chamber housing 96. In the illustrated embodiments, the air flow assembly 98 includes an inlet duct 112 that extends from the air inlet 70 to an aperture 114 defined in the side wall 102 of the sample chamber assembly 96. The air flow assembly 98 further includes a filter base 120 to which a filter 122 is coupled. In embodiments, the filter base 120 can be integral with a front wall 62, mounted to the front wall 62, mounted to the sample chamber assembly 96, and/or the like. Filter-pump tubing 124 extends from the filter 122 to a pump 126. In embodiments, the pump 126 provides the fluid motion of the air through the assembly 10 and can comprise any number of different types of pumps such as, for example, a micropump. In embodiments, the pump 126 is communicatively coupled to the controller 92, which controls the operation of the pump 126.

As shown, the air flow assembly 98 further includes pump-elbow tubing 132 that extends from a pump outlet 128 to a reduction elbow 134, and elbow-flow sensor tubing 136 that extends from the reduction elbow 134 to a flow sensor 138. In embodiments, the flow sensor 138 can be any type of mass flow sensor that measures the amount of air passing through the sensor 138. According to embodiments, the flow sensor 138 can be coupled to the sample chamber housing 96 via a sensor mount 142. In the illustrated embodiments, the sensor mount 142 is generally L-shaped, having a first portion 144 coupled to the rear wall 106 of the sample chamber housing 96 and a second portion 146, extending away from the sample chamber housing 96. The mass flow sensor 138 is coupled to the second portion 146 of the sensor mount 142. In embodiments, one or both of the portions 144 and 146 of the sensor mount 142 can include apertures 148 through which tubing can be passed. In embodiments, other types of mounts or attachment mechanisms can be used to dispose the flow sensor 138 within the housing 14. Additionally, in embodiments, the flow sensor 138 is communicatively coupled to the controller 92 and provides flow measurements to the controller 92. A sensor output 140 extends from the flow sensor 138 to the air outlet 72 (depicted in FIG. 1C).

According to embodiments, the air flow assembly 98 and portions of the sample chamber assembly 96 define an air flow path, as follows. In the illustrated embodiments, air enters the sampler assembly 10 through the air inlet 70 and flows through an inlet duct 112 into the sample chamber housing 96 via an aperture 114 defined in the side wall 102. The air enters the sample chamber 117 (shown in FIGS. 2A and 2B) through a first internal duct 116 (shown in FIGS. 2A and 2B) and exits the sample chamber 117 into a second internal duct 118 (shown in FIGS. 2A and 2B), which directs the air through the filter base 120 and into the filter 122. The air exits the filter 122 into the filter-pump tubing 124 and moves through the filter-pump tubing 124 and into the pump 126 via a pump inlet 128. In embodiments, the pump 126 provides the fluid motion of the air through the assembly 10. The air exits the pump 126 via a pump outlet 130 and travels through the pump-elbow tubing 132, through the reduction elbow 134 and into the elbow-flow sensor tubing 136. The elbow-flow sensor tubing 136 directs the air into the flow sensor 138. The air exits the flow sensor 138 through the flow sensor output 140 and is expelled into the ambient environment through the air outlet 72 (depicted in FIG. 1C).

Figure 2A:
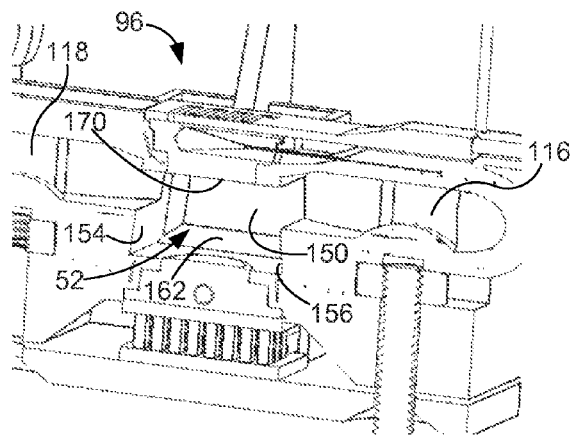
FIGS. 2A and 2B are cross-sectional perspective views of the thermophoretic sampler of FIGS. 1A and 1B in accordance with embodiments of the disclosure.
Figure 2C:
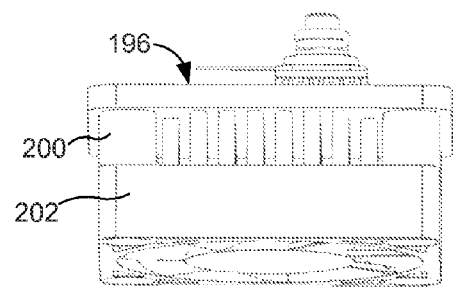
FIG. 2C is a perspective view of a cooling mechanism in accordance with embodiments of the disclosure.
Figure 2B:
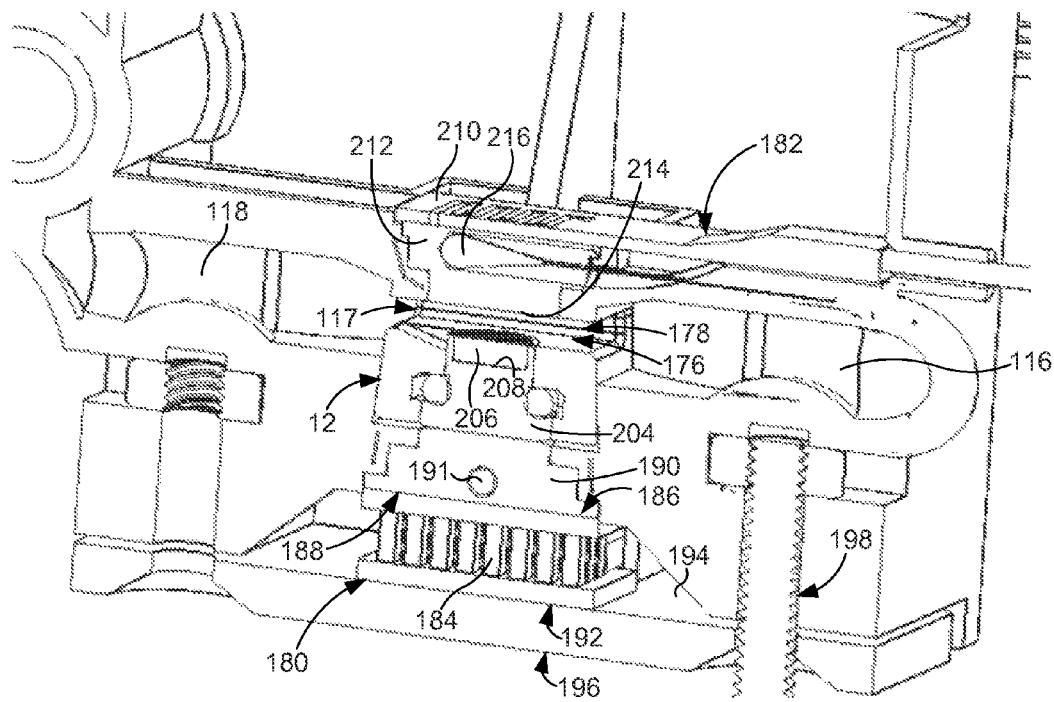

FIG. 2A shows a cross section of the sample chamber housing 96 in which the sample cartridge 12 has been removed and FIG. 2B shows a cross section of the sample chamber housing 96 in which the sample cartridge 12 is fully inserted. As shown in FIG. 2A, the sample chamber housing 96 includes a sample cartridge channel 52 configured to receive the first portion 54 of the sample cartridge 12. The sample cartridge channel 52 includes a stopping surface 150 that engages a front surface 152 of the sample cartridge (see FIG. 1D) when the sample cartridge 12 is fully inserted. The cartridge channel 52 further includes two opposed side surfaces 154 and 156 that are arranged to slideably engage two corresponding side surfaces 158 and 160 of the sample cartridge 12, respectively, as well as a lower surface 162 configured to slideably engage a lower surface 164 of the sample cartridge 12. An upper surface 166 (shown in FIG. 1C) of the cartridge channel 52 is configured to slideably receive an upper surface 168 of the sample cartridge 12.

As shown in FIG. 2A, an upper chamber boundary 170 corresponds to the notch 15 defined in the first portion 54 of the sample cartridge 12 such that, when the sample cartridge 12 is fully inserted into the cartridge channel 52, the sample chamber 117 is provided. The sample chamber 117 includes a void bounded, above, by the upper chamber boundary 170, and, below, by the internal surfaces 55 and 57 of the notch 15. The sample chamber 117 forms a portion of a flow of air through the sampler 1 within which thermophoresis is induced, thereby facilitating deposition of nanoparticles on the substrate 13. According to embodiments, the size and shape of the sample chamber 117 can be varied by varying the size and shape of the notch 15. In the illustrated embodiments, for example, the notch 15 is shown as having a rectangular shape, although other shapes such as ovular shapes, pentagonal shapes, and/or the like can be utilized in embodiments. Additionally, in embodiments, the internal surfaces 55 and 57 of the notch 15 can include any number of different features such as, for example, grooves, ramps, recesses, and/or the like. For instance, in embodiments, a recess 172 can be defined in the lower internal surface 55 of the notch 15 to enable a user to grasp the substrate 13 with forceps. According to embodiments, by varying the design of the notch 15, characteristics of air flow and nanoparticle collection associated with a sampler assembly 10 can be varied using a number of different sample cartridges 12.

According to embodiments, nanoparticle samples are collected on a collection surface 174 of the substrate 13, which is exposed to a first region 176 (e.g., "cold" region) of the sample chamber 117. During sampling, air enters the sample chamber 117 through the first internal duct 116, passes through the sample chamber 117 and exits the sample chamber 117 into a second internal duct 118. Thermophoresis is induced in the air within the sample chamber 117 by maintaining the substrate 13 at a temperature that is lower than a temperature of a second ("warm") region 178 of the sample chamber 117. The lower temperature of the substrate 13 is achieved using a cooling mechanism 180. In embodiments, the "warm" region 178 is heated using a heating mechanism 182, while in other embodiments, the "warm" region 178 has an ambient temperature with respect to which the substrate 13 is cooled. In the embodiments illustrated in FIGS. 2A and 2B, a heating mechanism 182 is used to apply heat to the "warm" region 178. According to embodiments, the temperature difference is regulated, using the controller 92, such that thermophoresis causes nanoparticles to move toward, and be deposited on, the substrate 13.

In embodiments, the cooling mechanism 180 includes a thermoelectric cooler 184 that is thermally coupled to the substrate 13. As discussed herein, two objects are "thermally coupled" when heat can transfer from one object to the other. For example, two thermally conductive objects can be thermally coupled by placing a surface of one object in physical contact with a surface of the other object. Additionally, for example, a first object can be thermally coupled to a second object by placing a third, thermally conductive, object between the first and second objects such that a surface of each of the first and second objects contacts a surface of the third object. Similarly, a first object and a second object can be thermally coupled even though a number of objects are disposed between them, so long as contacts are made between successive objects such that heat can be conducted from the first object to the second object, or vice versa. In embodiments, thermal coupling can be achieved by ensuring good physical contact between successive objects in a thermally conductive "stack" of such objects. Physical contact can be achieved between thermally conductive objects in any number of ways such as, for example, by applying pressure to the objects, fastening the objects together, and/or the like.

In the illustrated embodiments, the thermoelectric cooler 184 includes a first surface 186 that contacts a first surface 188 of a thermal conduction element 190 such that the thermoelectric cooler 184 can remove heat from the thermal conduction element 190. In embodiments, a temperature sensor 191 such as, for example a thermistor, is disposed within the first thermal conduction element 190 for monitoring the temperature thereof. In other embodiments, the temperature sensor 191 can be exposed to the sample chamber 117, disposed in the sample cartridge 12, and/or the like. In embodiments, temperature measurements can be received from the temperature sensor 191 by the controller 92 to facilitate regulation of temperature differentials.

The thermoelectric cooler 184 includes a second surface 192 that contacts a surface 194 of a heat dissipation mechanism 196, which, in embodiments, can include, or be integral with, the lower wall 108 of the sample chamber housing 96. In embodiments, the heat dissipation mechanism 196 removes heat from the thermoelectric cooler 184 to facilitate its operation. In embodiments, the thermoelectric cooler 184 and the thermal conduction element 190 can be held in contact, thereby facilitating thermal coupling, using a compression fastening mechanism 198 such as, for example, a combination of screws and compression springs, which may also hold the lower wall 108 of the sample chamber housing 96 in contact with the second surface 192 of the thermoelectric cooler 184. In embodiments, the heat dissipation mechanism 196 can include a thermally conductive material. For example, in some embodiments, the lower wall 108 can be integrated with other portions of the sample chamber housing 96, the sample core assembly housing 14, and/or the like, to further dissipate heat that is removed from the thermoelectric cooler 184. In some embodiments, as shown in FIG. 2C, the heat dissipation mechanism 196 can include a heat sink 200 and/or a fan 202 to further facilitate dissipation of heat.

As shown in FIG. 2B, a second thermal conduction element 204 is disposed within the first portion 54 of the sample cartridge 12. In embodiments, the second thermal conduction element 204 can be disposed within the sample chamber housing 96. In some embodiments, one thermal conduction element may be used, while, in other embodiments, two or more thermal conduction elements may be used. In the illustrated embodiments, thermal coupling is maintained between the thermoelectric cooler 184 and the first thermal conduction element 190, between the first and second thermal conduction elements 190 and 204, and between the second thermal conduction element 204 and the substrate 13. By maintaining physical contact between these elements, the thermoelectric cooler 184 can be thermally coupled to the substrate 13 and, thus, can remove heat from the substrate 13, thereby cooling the substrate 13 to maintain the temperature difference within the sample chamber 117. In the illustrated embodiments, a magnet 206 disposed on an upper surface 208 of the second thermal conduction element 204 holds a magnetic nanoparticle collection substrate 13 in place, and thermal coupling is also maintained between the substrate 13, the magnet 206, and the second thermal conduction element 204. In other embodiments, a non-magnetic substrate may be held in place using another means such as, for example, a mechanical means, in which case a magnet 206 may not be present and the upper surface 208 of the second thermal conduction element 204 can be held in contact with the substrate 13.

In the illustrated embodiments, the heating mechanism 182 includes a heating element 210 such as, for example, a resistive heater, that applies heat to a thermal conduction element 212 that is disposed in the sample chamber housing 96. A lower surface 214 of the thermal conduction element 212 can be exposed to the second region 178 of the sample chamber 117 and the heating element is thermally coupled to the thermal conduction element 212 to facilitate raising the temperature of the second ("warm") region 178. In embodiments, a temperature sensor 216 such as, for example a thermistor, can be disposed within the thermal conduction element 212 to monitor the temperature thereof. In other embodiments, the temperature sensor 216 can be exposed to the sample chamber 117, disposed in the sample cartridge 12, and/or the like. In embodiments, temperature measurements can be received from the temperature sensor 216 by the controller 92 to facilitate regulation of temperature differentials.

Figure 3A:
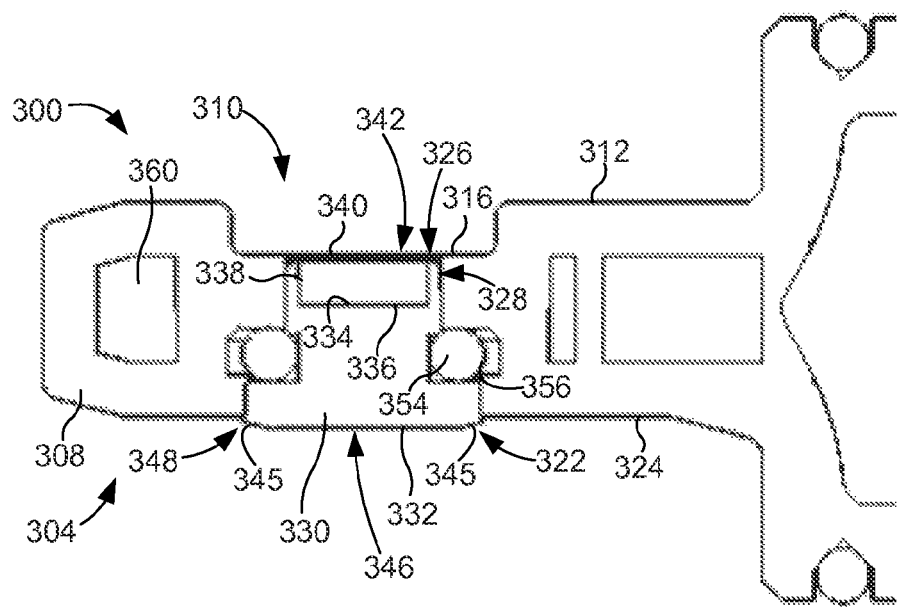
FIG. 3A is a cross-sectional side view of a sample cartridge in accordance with embodiments of the disclosure.
Figure 3B:
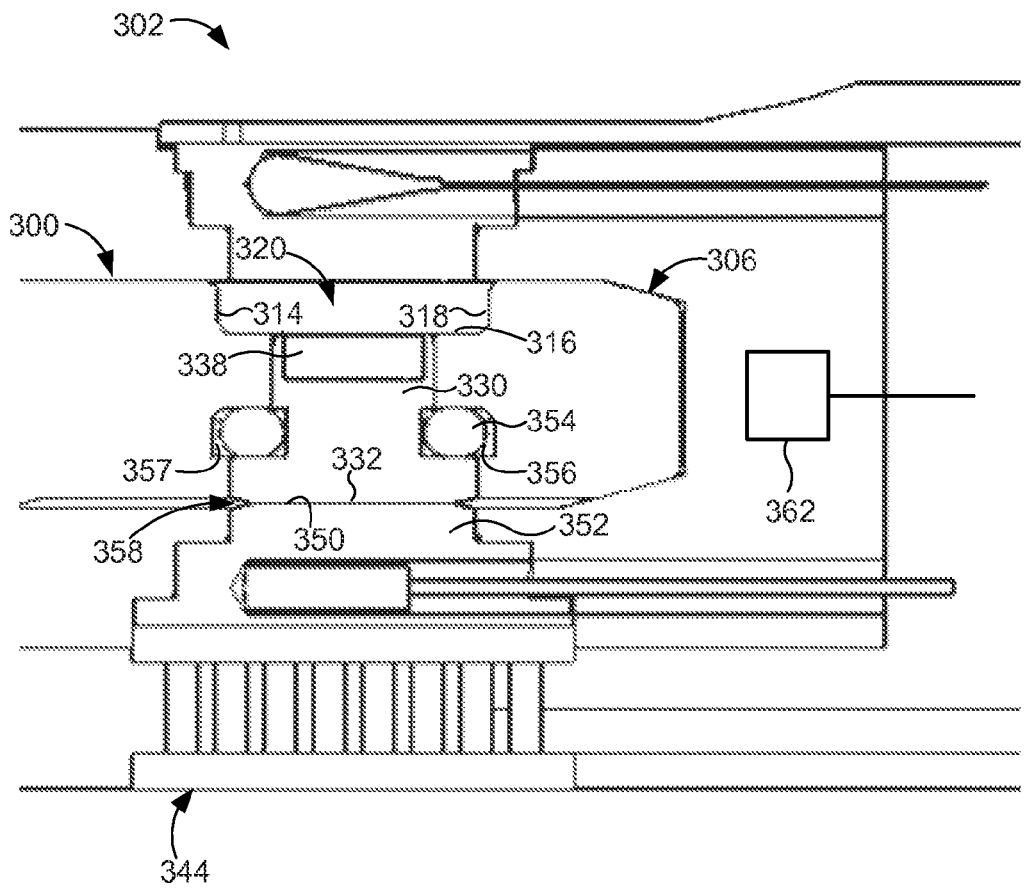
FIG. 3B is a cross-sectional side view of a sample chamber housing in accordance with embodiments of the disclosure.

FIGS. 3A and 3B depict a cross-sectional side view of an illustrative sample cartridge 300 and a sample chamber housing 302 having the cartridge 300 fully inserted, in accordance with embodiments of the disclosed subject matter. In embodiments, the sample cartridge 300 includes a first portion 304 configured to fit within a cartridge channel 306. As shown, the first portion 304 includes a body 308 having a notch 310 defined in an upper wall 312. In embodiments, as shown, for example, in FIG. 3B, internal surfaces 314, 316, and 318 of the notch 310 define a portion of the sample chamber 320 when the cartridge 300 is fully inserted into the cartridge channel 306.

In embodiments, the first portion 304 of the cartridge 300 has an opening 322 defined in the bottom surface 324, an opening 326 defined in the internal surface 316 of the notch 310 and a hollow channel 328 extending between the two openings 322 and 326. A first thermal conduction element 330 is disposed within the channel 328 such that a lower surface 332 of the first thermal conduction element 330 extends from the opening 322 and an upper surface 334 of the first thermal conduction element 330 contacts a lower surface 336 of a thermally conductive magnet 338. The magnet 338 is configured to hold a magnetic substrate 340, which is disposed within the opening 326. An upper surface 342 of the substrate 340 is used as a collection surface and the first thermal conduction element 330, the magnet 338, and the substrate 340 are all thermally coupled.

According to embodiments, to facilitate seating the sample chamber from the ambient environment such that air only enters the sample chamber through the air flow path, the sample cartridge 300 is configured to fit snugly within the cartridge channel 306. In embodiments, to further facilitate this seal, as well as to facilitate thermal coupling between a cooling mechanism 344 and the substrate 340, the lower surface 332 of the first thermal conduction element 330 includes an angled feature 345 such that an interior portion 346 of the lower surface 332 extends downward farther than the periphery 348. For example, as shown in FIGS. 3A and 3B, the angled feature 345 can include a beveled edge extending annularly around the periphery 348 of the lower surface 332 of the first thermal conduction element 330. When the cartridge 300 is inserted into the cartridge channel 306, the angled feature 345 engages an upper surface 350 of a second thermal conduction element 352, causing an upward force on the thermal conduction element 330. An elastic mechanism 354 (e.g., a spring, an elastomeric o-ring, and/or the like), partially disposed within a recess 356 defined in the cartridge 300 and partially disposed within a recess 357 defined within the first thermal conduction element 330, compresses in response to the upward force, thereby facilitating contact between the second thermal conduction element 352, the first thermal conduction element 330, the magnet 338, and the substrate 340, which, in embodiments, enables thermal coupling between the second thermal conduction element 352 and the substrate 340. According to embodiments, the upper surface 350 of the second thermal conduction element 352 may also include an angled feature 358.

According to embodiments of the disclosed subject matter, the cartridge 300 may include one or more communication components. For example, in embodiments, the cartridge 300 may include a radio-frequency identification (RFID) tag 360 that can be read by an RFID sensor 362 disposed in the sample chamber housing 302. In embodiments, other types of wired or wireless communication components can be integrated with the cartridge 300 and/or the sampler assembly such as, for example, USB components, BLUETOOTH® components, and/or the like. Communications between the cartridge 300 and the sampler assembly can be used to transfer information related to users, samples, sample processes, instructions for sampling, ambient condition measurements, and/or the like.

FIGS. 4A-4D show another illustrative sample cartridge 400 in accordance with embodiments of the disclosed subject matter. The illustrative cartridge 400 retains a substrate 402 mechanically. Thus, for example, in embodiments, the illustrative cartridge 400 can be used to hold substrates 402 that do not include magnetic material. As shown, the cartridge 400 includes a notch 404 defined in an upper surface 406. A retaining wall 408 is disposed within the notch 404 and is configured to engage at least a portion of a periphery 410 of the substrate 402. In embodiments, the retaining wall 408 has a shape that corresponds to the shape of the outside periphery 410 of the substrate 402. A first deflection feature 412 is provided on a first side of the notch 404 and a second deflection feature 414 is provided on a second side of the notch 404. The deflection features 412 and 414 provide a force on an upper surface 418 of the substrate 402, thereby causing a downward force on the substrate 402. When the cartridge 400 is fully inserted into a sampler assembly, this downward force opposes the upward force on a thermal conduction element 420 (described, for example, above), thereby facilitating thermal coupling between the thermal conduction element 420 and the substrate 402. An elastic mechanism 422 (e.g., a spring, an elastomeric o-ring, and/or the like) is disposed partially within a recess 424 defined within the cartridge 400 and partially within a recess 426 defined within the thermal conduction element 420, and can, in embodiments, facilitate thermal coupling of the thermal conduction element 420 and the substrate 402. Additionally, in embodiments, the configuration of the deflection features 412 and 414 enables a user to slide the substrate 402 into, and out of, engagement with the cartridge 400.

In the illustrated embodiments, each deflection feature 412 and 414 includes an arm 430 that curves (or otherwise turns), thereby defining a void 432 between an inside surface 434 of the arm 430 and an inside surface 436 of the notch 404. The arm 430 includes a first portion 440 extending toward the center 442 of the substrate 402 with a generally parallel orientation with respect to the upper surface 418 of the substrate 402. The arm 430 includes a second portion 444 extending toward the upper surface 418 with a generally perpendicular orientation with respect to the upper surface 418 of the substrate 402. A tab 446 extends from the end of the second portion 444 at least partially away from the center 442 of the substrate 402 and engages the upper surface 418 of the substrate 402, as shown, for example, in FIG. 4D. In embodiments, the deflection features 412 and 414 can be created by boring a hole (e.g., the void 432) near the top of each inside surface 436 of the notch 404. In other embodiments, the deflection features 412 and 414 can be created during a molding process for creating the cartridge 400. Additionally, according to embodiments, the deflection features 412 and 414 can include any number of different configurations suitable for engaging a portion of a substrate 404 and providing a force on the substrate 404 that facilitates maintenance of thermal coupling between the substrate 404 and the thermal conduction element 420.

Figure 5A:
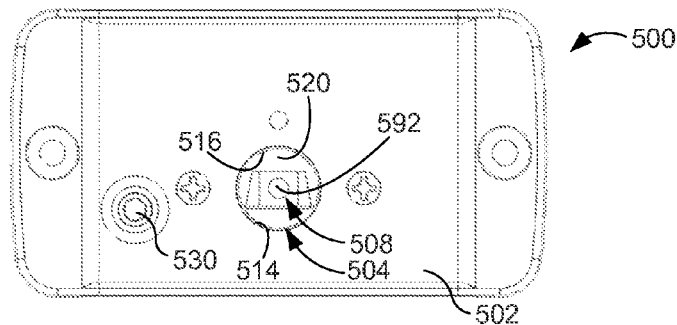
FIGS. 5A-5C are perspective views of a sample core assembly in accordance with embodiments of the disclosure.
Figure 5B:
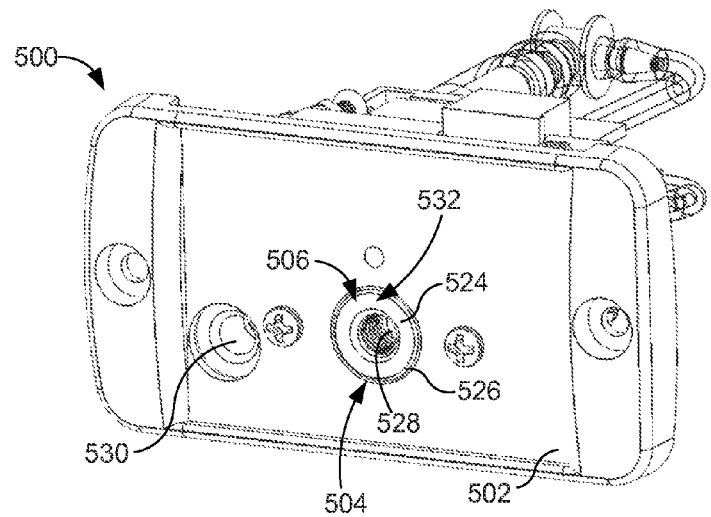
Figure 5C:
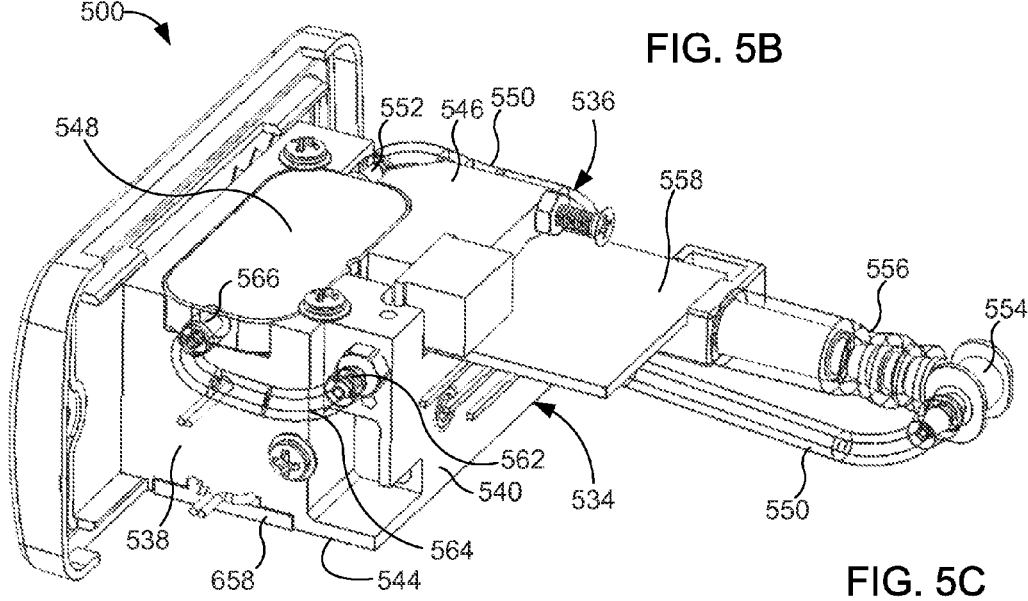

Embodiments of the disclosed subject matter include a thermophoretic sampler similar to the sampler described above, with reference to FIGS. 1A-4D, but having the air inlet disposed within the sample cartridge. According to embodiments, the sampler having the sample core assembly 500 may include any one or more of the other features of the sampler 10 described above. FIG. 5A is a front view of a sample core assembly 500 of a thermophoretic sampler having a front plate 502 disposed thereon, in accordance with embodiments of the disclosure. FIGS. 5B and 5C are perspective views of the sample core assembly 500 in accordance with embodiments of the disclosure. In embodiments, the sample core assembly 500 may be disposed within a housing (not shown) such as, for example, the housing 14 depicted in FIGS. 1A and 1B. As shown in FIGS. 5A and 5B, a front plate 502 includes a cartridge port 504 for receiving a sample cartridge 506 (shown, in more detail, in FIGS. 7A-7C). As shown, a cartridge channel 508 extends from the cartridge port 504 into the sampler core assembly 500 and is configured for receiving a first portion 510 of the sample cartridge 506, which includes a substrate 512. In the illustrated embodiments, the cartridge channel 508 has a generally trapezoidal shape, which corresponds to a generally trapezoidal shape of the first portion 510 of the sample cartridge. According to embodiments, the cartridge channel 508 and the first portion 510 of the cartridge 506 can be configured according to other shapes, depending on the details of the implementation, such as, for example, rectangular shapes, circular shapes, triangular shapes, pentagonal shapes, and/or the like.

As shown, the cartridge port 504 includes a first surface 514 extending from the front plate 502 to a stopping surface 516, which may lie in a plane substantially parallel to the front plate 502. According to embodiments, when the sample cartridge 506 is fully inserted through the cartridge port 504, the stopping surface 516 engages a surface 518 on the sample cartridge 506 and a second stopping surface 520, defined within the cartridge port 504, engages a second surface 522 on the sample cartridge 506. In this fully inserted position, a sealing portion 524 of the sample cartridge 506 engages a sealing assembly 526 of the cartridge port 504 to create a seal from the outside environment. In embodiments, the sealing portion 524 of the sample cartridge 506 and/or the sealing assembly 526 of the cartridge port 504 may include one or more sealing mechanisms such as, for example, o-rings, gaskets, and/or the like. When the sample cartridge 506 is fully inserted, thereby causing the cartridge port 504 to be sealed from the outside environment, air enters and exits the sampler core assembly 500 through an air inlet 528 and an air outlet 530, respectively. As shown in FIGS. 5A and 5B, the air inlet 528 is disposed in a first end 532 of the sample cartridge 506.

As depicted in FIG. 5C, the sample core assembly 500 includes a sample chamber housing 534 and an air flow assembly 536. The sample chamber housing 534 includes side walls 538, a rear wall 540, a front wall 542 (as shown in FIG. 5D), a lower wall 544, and an upper wall 546. The air flow assembly 536 provides a portion of an air flow path through the sampler core assembly 500. According to embodiments, any number of different types of air flow assemblies can be used to facilitate moving air through the sample chamber housing 534. In the illustrated embodiments, the air flow assembly 536 includes a pump 548. In embodiments, the pump 548 provides the fluid motion of the air through the sample core assembly 500 and can comprise any number of different types of pumps such as, for example, micropump, and may be similar to the pump 126 depicted in FIGS. 1G and 1H.

As shown, the air flow assembly 536 further includes pump-elbow tubing 550 that extends from a pump outlet 552 to a reduction elbow 554, and elbow-flow sensor tubing 556 that extends from the reduction elbow 554 to a flow sensor 558. In embodiments, the flow sensor 558 can be any type of mass flow sensor that measures the amount of air passing through the sensor 558 and may be similar to the flow sensor 138 depicted in FIGS. 1G and 1H. In embodiments, sensor mounts such as, for example, the sensor mount 142 depicted in FIGS. 1G and 1H may be used to couple the flow sensor 558 to the sample core housing 534. In embodiments, other types of mounts or attachment mechanisms can be used to dispose the flow sensor 558 within the sampler housing. A sensor output (not shown) extends from the flow sensor 558 to the air outlet 530.

According to embodiments, the air flow assembly 536 and portions of the sample chamber housing 534 define an air flow path. In the illustrated embodiments, air enters the sampler core assembly 500 through the air inlet 528 and flows directly into the sample chamber 560 (shown in FIGS. 6A-6D). Any number of various internal channels, filters, and/or the like, may be disposed within the sample chamber housing 534. The air exits the sample chamber housing 534 via housing outlet 562 into the housing-pump tubing 564 and moves through the housing-pump tubing 564 and into the pump 548 via a pump inlet 566. The air exits the pump 548 via the pump outlet 552 and travels through the pump-elbow tubing 550, through the reduction elbow 554 and into the elbow-flow sensor tubing 556. The elbow-flow sensor tubing 556 directs the air into the flow sensor 558. The air exits the flow sensor 558 through a flow sensor output (not shown) and is expelled into the ambient environment through the air outlet 530.

FIG. 5D shows a perspective view of the sample chamber housing 534 having a sample cartridge 506 disposed therein, in accordance with embodiments of the disclosure. FIG. 5E shows an exploded view of the sample chamber housing 534 without the sample cartridge 506, in accordance with embodiments of the disclosure. As shown in FIGS. 5D and 5E, the sample chamber housing 534 includes a first sample core insert 568 configured to be inserted into a recess 570 disposed in the bottom wall 544 of the sample chamber housing 534. A second sample core insert 572 is configured to be disposed below the first sample core insert 568, also within the recess 570. The first sample core insert 568 includes a channel 574 that, when closed from the bottom by the upper surface 576 of the second sample core insert 572, creates the cartridge channel 508 described above.

As shown in FIG. 5E and FIG. 5F (which depicts an inverted first sample core insert 568 in accordance with embodiments of the disclosure), the channel 574 is defined by an upper surface 578, a first side 580, a second side 582, and an internal surface 584. A first curved surface 586 is disposed between the first side 580 and the internal surface 584; and a second curved surface 588 is disposed between the second side 582 and the internal surface 584. According to embodiments, the first and second curved surfaces 586 and 588 may be configured to clear the leading corners of the sample cartridge 506 when it is fully inserted and may be configured to allow the first sample core insert 568 to be machined. In embodiments, the first sample core insert 568 may be injection molded and, in that case, the first sample core insert 568 may not include the first and second curved surfaces 586 and 588.

As is further shown in FIGS. 5E and 5F, the channel 574 is defined in a body 590 of the first sample core insert 568. The body 590 may have a half-cylinder shape, as shown. In embodiments, the body 590 may be configured with any number of other shapes and/or combinations of shapes. A first aperture 592 may be disposed in the internal surface 584 and, in operation, may allow air to flow out of the sample chamber 560. A second aperture 594 may be disposed in the upper surface 578 of the channel 574 and may be configured to allow for a thermal conduction element 668 to be disposed therein such that the thermal conduction element 668 may be exposed to the sample chamber 560. A first end surface 596 may, in embodiments, be configured to function as the second stopping surface 520 described above, with regard to FIG. 5A. In embodiments, a stopper (e.g., a ring, washer, etc.) may be configured to engage a portion of the first end surface 596 to function as the second stopping surface 520.

Additionally, as shown, the first sample core insert 568 may include a flange 598 disposed at an internal end 600 of the first sample core insert 568 and extending downward from a lower surface 602 of the body 590. This flange 598 may, in embodiments, facilitate creating a space 604 (as shown, e.g., in FIG. 6B) in the sample chamber housing 534 that may be, e.g., an empty air space, filled with an insulating material, and/or the like. In this manner, the space 604 may facilitate reducing thermal convection to the thermoelectric cooler 644 (described below). As shown, an aperture 606 may be defined through the second sample core insert 572 to facilitate exposure of a thermal conduction element 650 to the sample cartridge 506 to facilitate thermal coupling of the substrate 512 with a cooling mechanism 640. In embodiments, at least a portion of the second sample core insert 572 may be configured to engage the lower surface 602 of the body 590 of the first sample core insert 568 to form the cartridge channel 508.

Figure 6A:
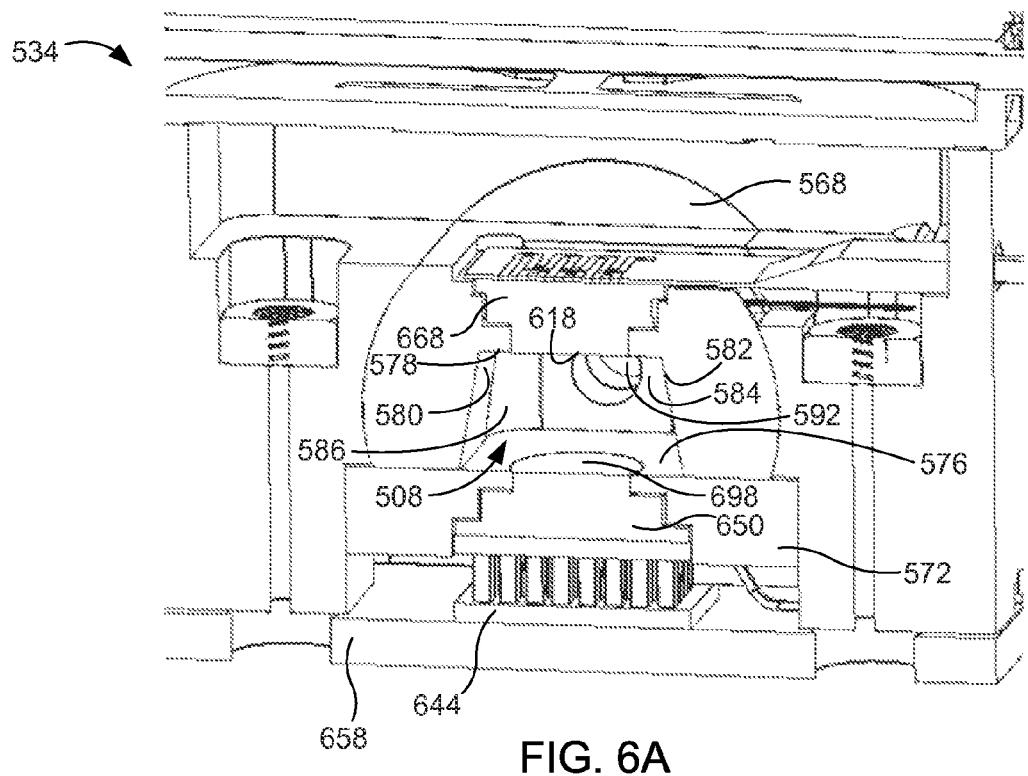
FIGS. 6A and 6B are cross-sectional perspective views of a sample chamber housing in accordance with embodiments of the disclosure.
Figure 6B:
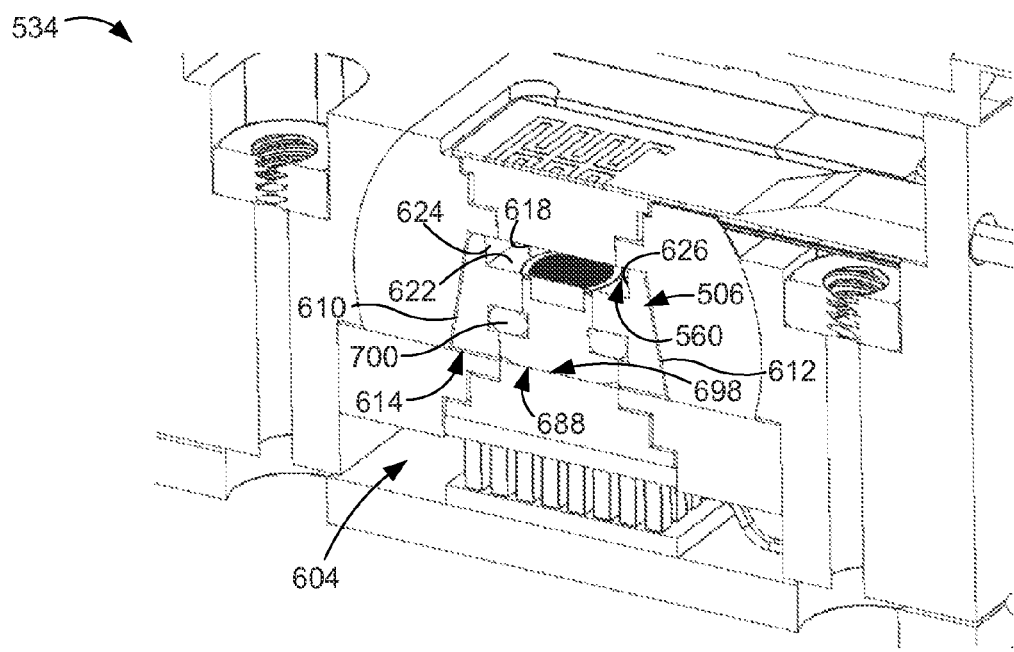
Figure 6C:
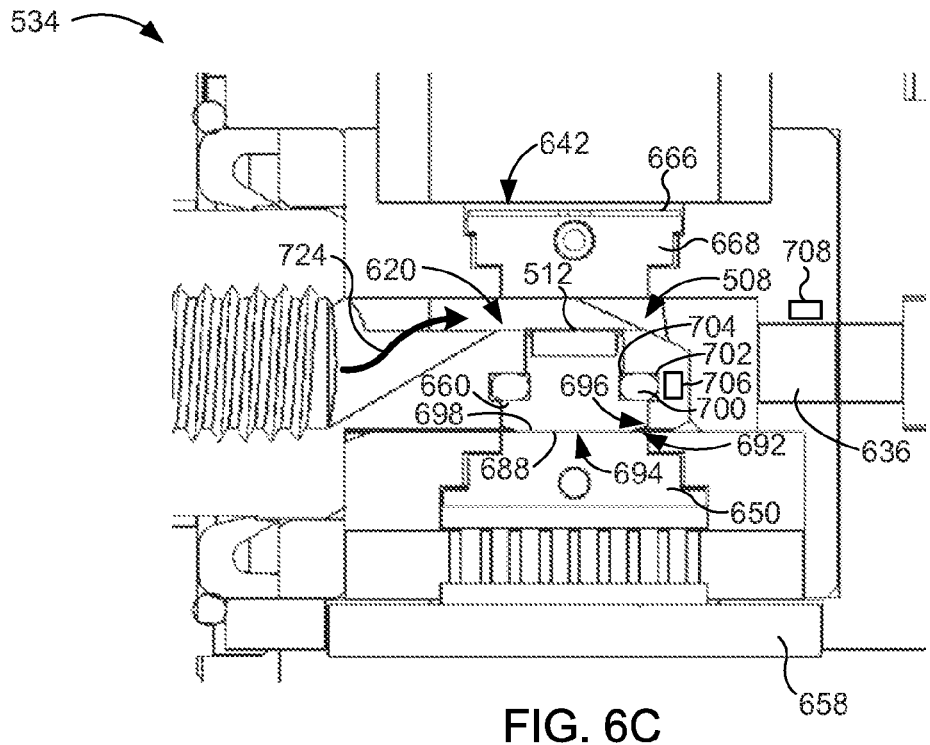
FIG. 6C is a cross-sectional side view of a sample chamber housing in accordance with embodiments of the disclosure.
Figure 6D:
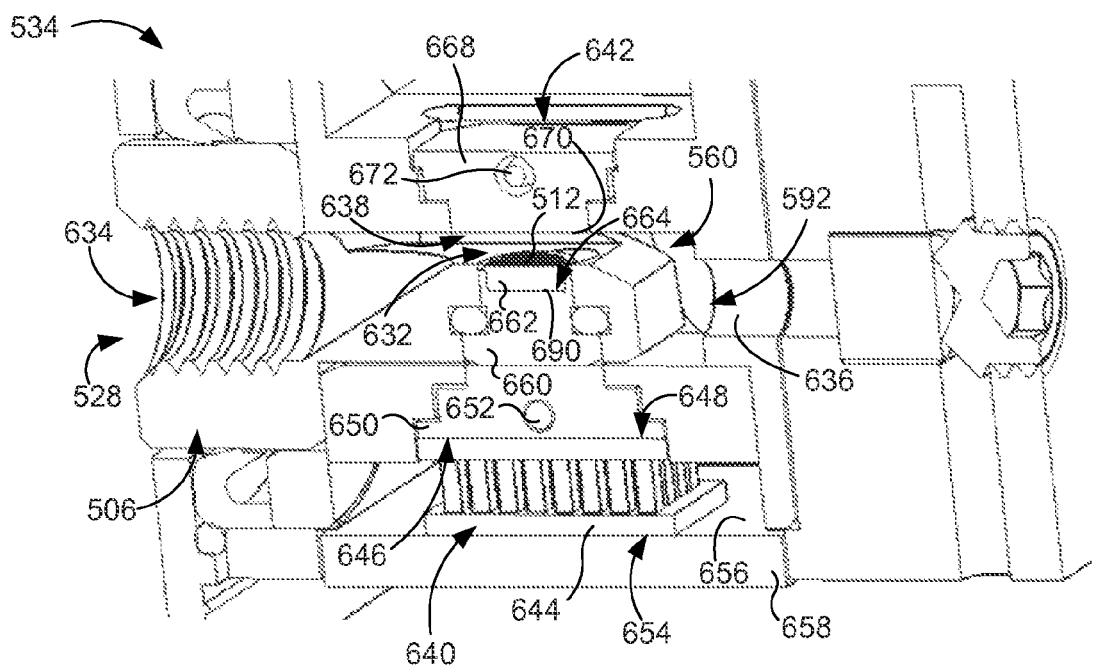
FIG. 6D is a cross-sectional perspective view of a sample chamber housing in accordance with embodiments of the disclosure.
Figure 7A:
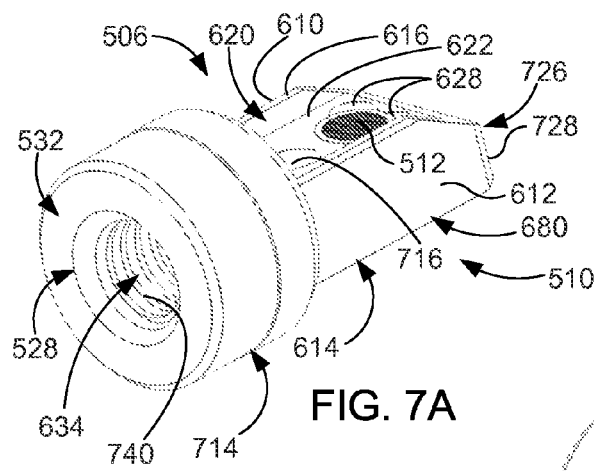
FIGS. 7A and 7B are perspective views of a sample cartridge in accordance with embodiments of the disclosure.
Figure 7B:
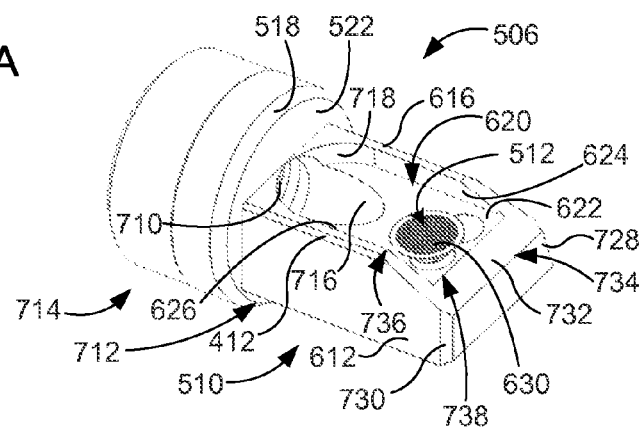
Figure 7C:
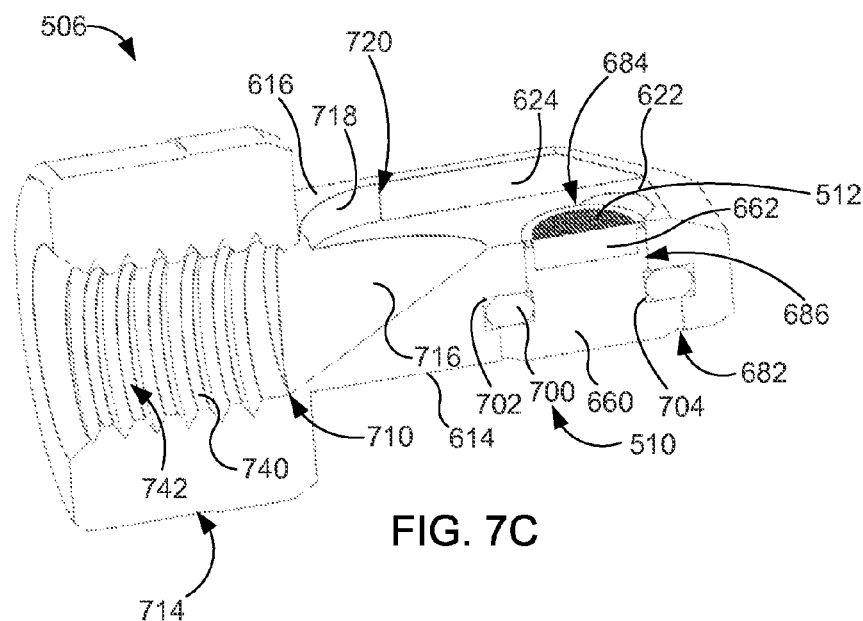
FIG. 7C is a cross-sectional perspective view of a sample cartridge in accordance with embodiments of the disclosure.

Aspects of the following discussion of embodiments of the disclosure are depicted in FIGS. 6A-6D and 7A-7C. FIG. 6A shows a cross section of the sample chamber housing 534 in which the sample cartridge 506 has been removed, and FIGS. 6B-6D show various views of a cross section of the sample chamber housing 534 in which the sample cartridge 506 is fully inserted. Additionally, FIGS. 7A and 7B depict perspective views of an illustrative sample cartridge 506, in accordance with embodiments of the disclosed subject matter. FIG. 7C depicts a cross-sectional perspective view of the sample cartridge 506, in accordance with embodiments of the disclosed subject matter. As shown in FIG. 6A, the sample chamber housing 534 includes a sample cartridge channel 508 configured to receive the first portion 510 of the sample cartridge 506. The cartridge channel 508 includes two opposed side surfaces 580 and 582 that are arranged to slidably engage two corresponding side surfaces 610 and 612 of the sample cartridge 506, respectively, as well as a lower surface 576 configured to slidably engage a lower surface 614 of the sample cartridge 506. An upper surface 578 of the cartridge channel 508 is configured to slideably receive an upper surface 616 of the sample cartridge 506. As shown, for example, in FIGS. 7A-7C, the upper surface 616 may be, or include an upper edge of a corresponding side 610 or 612.

An upper chamber boundary 618 corresponds to a notch 620 defined in the first portion 510 of the sample cartridge 506 such that, when the sample cartridge 506 is fully inserted into the cartridge channel 508, the sample chamber 560 is provided. The sample chamber 560 includes a void bounded in part, above, by the upper chamber boundary 618, and, below, by the internal surfaces 622, 624, and 626 of the notch 620. The sample chamber 560 forms a portion of a flow of air through the sampler within which thermophoresis is induced, thereby facilitating deposition of nanoparticles on the substrate 512. According to embodiments, the size and shape of the sample chamber 560 can be varied, e.g., by varying the size and shape of the notch 620. Additionally, in embodiments, the internal surfaces 622, 624, and 626 of the notch 620 can include any number of different features such as, for example, grooves, ramps, recesses, and/or the like. For instance, in embodiments, one or more recesses 628 can be defined in the tower internal surface 622 of the notch 620 to enable a user to grasp the substrate 512 with forceps. According to embodiments, by varying the design of the notch 620, characteristics of air flow and nanoparticle collection associated with a sampler assembly can be varied using a number of different sample cartridges 506.

According to embodiments, the operation of embodiments of the sampler having the air inlet disposed within the sample cartridge is similar to that of embodiments of the sampler described above with the separate air inlet. That is, in embodiments, samples (e.g., nanoparticle samples) are collected on a collection surface 630 of the substrate 512, which is exposed to a first region 632 (e.g., "cold" region) of the sample chamber 560. During sampling, air enters the sampler through the air inlet 528, passes into the sample chamber 560 through an inlet duct 634 defined in the sample cartridge 506, passes through the sample chamber 560 and exits the sample chamber 560, via the aperture 592, into an internal duct 636. Thermophoresis is induced in the air within the sample chamber 560 by maintaining the substrate 512 at a temperature that is lower than a temperature of a second ("warm") region 638 of the sample chamber 560. The lower temperature of the substrate 512 is achieved using a cooling mechanism 640. In embodiments, the "warm" region 638 is heated using a heating mechanism 642, while in other embodiments, the "warm" region 638 has an ambient temperature with respect to which the substrate 560 is cooled. According to embodiments, the temperature difference is regulated in the manner described above with reference to embodiments depicted in FIGS. 1A-2B (e.g., by using a controller), such that thermophoresis causes nanoparticles to move toward, and be deposited on, the substrate 512.

In embodiments, the cooling mechanism 640 may be, be similar to, or include, the cooling mechanism 180 described above with reference to FIGS. 2A and 2B. That is, for example, the cooling mechanism 650 may include a thermoelectric cooler 644 that is thermally coupled to the substrate 512. In the illustrated embodiment, the thermoelectric cooler 644 includes a first surface 646 that contacts a first surface 648 of a thermal conduction element 650 such that the thermoelectric cooler 644 can remove heat from the thermal conduction element 650. In embodiments, a temperature sensor 652 such as, for example a thermistor, is disposed within the first thermal conduction element 650 for monitoring the temperature thereof. In other embodiments, one or more temperature sensors 652 can be exposed to the sample chamber 560, disposed in the sample cartridge 506, and/or the like. In embodiments, temperature measurements can be received from the temperature sensor 652 by the controller (e.g., the controller 92 depicted FIG. 1F) to facilitate regulation of temperature differentials.

The thermoelectric cooler 644 includes a second surface 654 that contacts a surface 656 of a heat dissipation mechanism 658, which, in embodiments, may be coupled to, include, or be integral with, the lower wall 544 of the sample chamber housing 534. In embodiments, the heat dissipation mechanism 658 removes heat from the thermoelectric cooler 644 to facilitate its operation. In embodiments, the thermoelectric cooler 644 and the thermal conduction element 650 can be held in contact, thereby facilitating thermal coupling, using any number of mechanisms such as, for example a compression fastening mechanism (e.g., the compression fastening mechanism 198 depicted in FIG. 2B). In embodiments, the heat dissipation mechanism 658 may be, be similar to, or include the heat dissipation mechanism 196 depicted in FIG. 2B, and may include a thermally conductive material, a heat sink, a fan and/or the like, to further facilitate dissipation of heat.

As shown in FIGS. 6B-6D and 7C, a second thermal conduction element 660 is disposed within the first portion 510 of the sample cartridge 506. In embodiments, the second thermal conduction element 660 can be disposed within the sample chamber housing 534. In embodiments, one thermal conduction element may be used, while, in other embodiments, two or more thermal conduction elements may be used. In the illustrated embodiments, thermal coupling is maintained between the thermoelectric cooler 644 and the first thermal conduction element 650, between the first and second thermal conduction elements 650 and 660, and between the second thermal conduction element 660 and the substrate 512. By maintaining physical contact between these elements, the thermoelectric cooler 644 can be thermally coupled to the substrate 512 and, thus, can remove heat from the substrate 512, thereby cooling the substrate 512 to maintain the temperature difference within the sample chamber 560. In the illustrated embodiments, a magnet 662 disposed on an upper surface 664 of the second thermal conduction element 660 holds a magnetic nanoparticle collection substrate 512 in place, and thermal coupling is also maintained between the substrate 512, the magnet 662, and the second thermal conduction element 660. In other embodiments, a non-magnetic substrate may be held in place using another means such as, for example, a mechanical means, in which case a magnet 662 may not be present and the upper surface 664 of the second thermal conduction element 660 can be held in contact with the substrate 512.

In the illustrated embodiments, the heating mechanism 642 includes a heating element 666 such as, for example, a resistive heater, that applies heat to a thermal conduction element 668 that is disposed in the sample chamber housing 534. A lower surface 670 of the thermal conduction element 668 can be exposed to the second region 638 of the sample chamber 560 and the heating element 666 is thermally coupled to the thermal conduction element 668 to facilitate raising the temperature of the second ("warm") region 638. In embodiments, a temperature sensor 672 such as, for example a thermistor, can be disposed within the thermal conduction element 668 to monitor the temperature thereof. In other embodiments, the temperature sensor 672 can be exposed to the sample chamber 560, disposed in the sample cartridge 506, and/or the like. In embodiments, temperature measurements can be used to facilitate regulation of temperature differentials.

In embodiments, as explained above, and as shown in FIGS. 7A-7C, the sample cartridge 506 includes a first portion 510 configured to fit within a cartridge channel 508. As shown, the first portion 512 includes a body 680 having a notch 620 defined in an upper wall 616. In embodiments, internal surfaces 622, 624, and 626 of the notch 620 define a portion of the sample chamber 560 when the cartridge 506 is fully inserted into the cartridge channel 508. In embodiments, the first portion 510 of the cartridge 506 has an opening 682 defined in the bottom surface 614, an opening 684 defined in the internal surface 622 of the notch 620 and a hollow channel 686 extending between the two openings 682 and 684. The second thermal conduction element 660 (described above) is disposed within the channel 686 such that a lower surface 688 of the second thermal conduction element 660 extends from the opening 682 and an upper surface 664 of the second thermal conduction element 660 contacts a lower surface 690 of the thermally conductive magnet 662. The magnet 662 may be configured to hold a magnetic substrate 512, which is disposed within the opening 684. In embodiments, an upper surface 630 of the substrate 512 is used as a collection surface and the second thermal conduction element 660, the magnet 662, and the substrate 512 are all thermally coupled.

According to embodiments, as with the embodiments described above, with reference to FIGS. 3A and 3B, to facilitate sealing the sample chamber 560 from the ambient environment such that air only enters the sample chamber through the air flow path, the sample cartridge 506 may be configured to fit snugly within the cartridge channel 508. In embodiments, to further facilitate this seal, as well as to facilitate thermal coupling between a cooling mechanism 640 and the substrate 512, the lower surface 688 of the second thermal conduction element 660 includes an angled feature 692 such that an interior portion 694 of the lower surface 688 extends downward farther than the periphery 696. For example, as shown in FIGS. 6C and 6D, the angled feature 692 may include a beveled edge extending annularly around the periphery 696 of the lower surface 688 of the second thermal conduction element 660. When the cartridge 506 is inserted into the cartridge channel 508, the angled feature 692 engages an upper surface 698 of the thermal conduction element 650, causing an upward force on the thermal conduction element 660. An elastic mechanism 700 (e.g., a spring, an elastomeric o-ring, or the like), partially disposed within a recess 702 defined in the cartridge 506 and partially disposed within a recess 704 defined within the second thermal conduction element 660, compresses in response to the upward force, thereby facilitating contact between the thermal conduction element 650, the second thermal conduction element 660, the magnet 662, and the substrate 512, which, in embodiments, enables thermal coupling between the thermal conduction element 650 and the substrate 512. According to embodiments, the upper surface 698 of the thermal conduction element 650 may also include an angled feature.

According to embodiments of the disclosed subject matter, the cartridge 506 may include one or more communication components. For example, in embodiments, the cartridge 506 may include a radio-frequency identification (RFID) tag 706 that can be read by an RFID sensor 708 disposed in the sample chamber housing 534. In embodiments, other types of wired or wireless communication components can be integrated with the cartridge 506 and/or the sampler assembly such as, for example, USB components, BLUETOOTH® components, and/or the like. Communications between the cartridge 506 and the sampler assembly can be used to transfer information related to users, samples, sample processes, instructions for sampling, ambient condition measurements, and/or the like.

As described above, in embodiments, an air inlet 528 is disposed at a first end 532 of the sample cartridge 506. In this manner, air may be pulled directly from the environment into the sample chamber 560 to be sampled. As shown, for example, in FIGS. 7A-7C, an inlet duct 634 extends from the air inlet 528, in a direction away from the first end 532, to an aperture 710 defined in a second end 712 of a second portion 714 of the sample cartridge 506. As shown in FIGS. 7A-7C, a depression 716 extends from the aperture 710 in a direction that is partially away from the first end 532, and a partially upward direction (e.g., away from the bottom surface 614). In embodiments, the depression 716 is at least partially defined within the lower internal surface 622 of the notch 620. The depression, as shown in FIGS. 7A-7C may also be partially defined in a curved surface 718 that extends from an end 720 of a first internal side surface 624 to the depression 716 and from the depression 716 to an end 722 of a second internal side surface 626. The size and shape (e.g., curvature, profile, etc.) of the depression 716 may be configured to facilitate desired characteristics of the air flow 724. Additionally, the degree of incline from the horizontal (defined as a plane parallel to a plane in which the bottom surface 614 of the sample cartridge 506 and/or the lower internal surface 622 of the notch 620 lies) may be similarly configured to facilitate desired air flow characteristics.

Additionally, to facilitate air flow characteristics, an end 726 of the first portion 510 of the sample cartridge 506 may be configured in any number of different ways. For example, as shown in FIGS. 7A-7C, the sample cartridge 506 may include a front surface 728, beveled corners 730 disposed between the front surface and each side surface 610 and 612, and an angled surface 732 extending, in part, from a top edge 734 of the front surface 728 to an end 736 of the upper surface 616, and, in part, from the top edge of 734 of the front surface 728 to an edge 738 of the lower internal surface 622 of the notch 620. Any number of other configurations of the sample cartridge 506 may be employed to facilitate air flow characteristics, in accordance with embodiments of the disclosure.

Figure 7D:
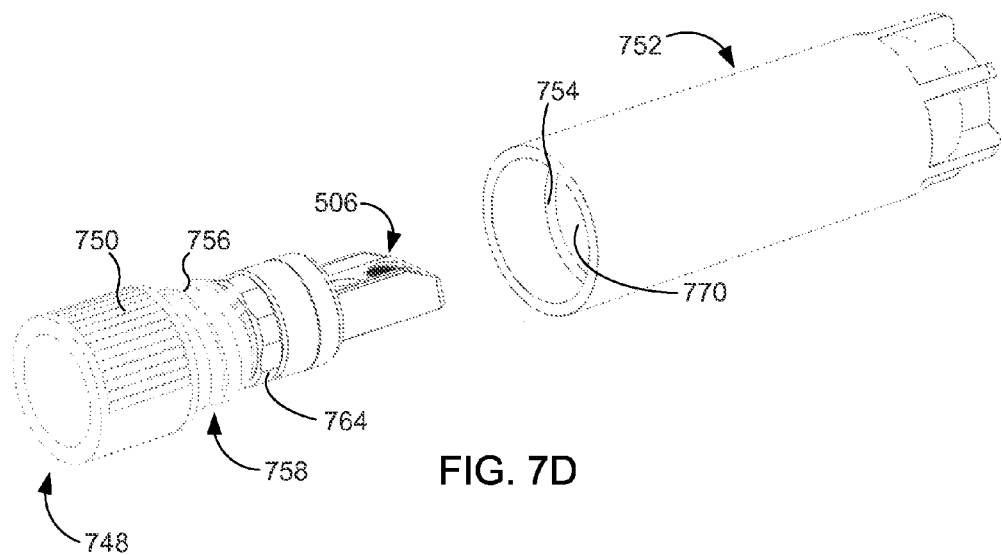
FIG. 7D is a perspective view of a container, and a sample cartridge coupled to a handle device, in accordance with embodiments of the disclosure.
Figure 7E:
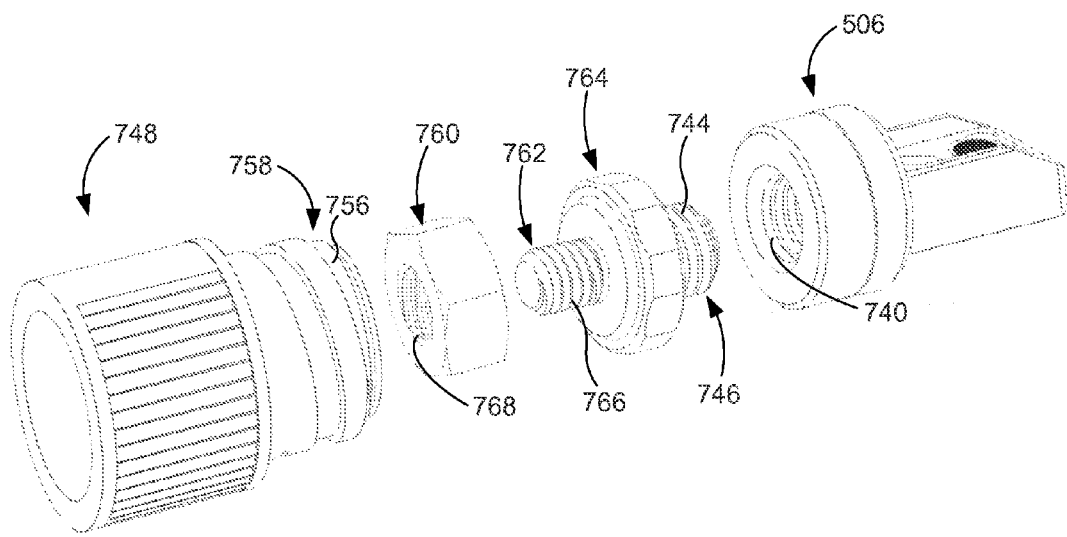
FIG. 7E is a perspective exploded view of the handle device shown in proximity to the sample cartridge of FIG. 7D, in accordance with embodiments of the disclosure.

According to embodiments, the sample cartridge 506 includes threading 740 disposed on an internal surface 742 of the inlet duct 634. As shown in FIGS. 7D and 7E, the threading 740 may be configured to mate with a first threading 744 disposed on a first exterior portion 746 of a handle device 748. In this manner, the handle device 748 may be screwed into the inlet duct 634 of the sample cartridge 506 to provide a handle that can be gripped by a user for facilitating insertion and removal of the sample cartridge 506. In embodiments, the handle can include any number of various types of grip features 750 to facilitate gripping by a user. According to embodiments, the threads 740 may also, or alternatively, be used to couple (e.g., via a corresponding set of threads) an air flow tube (not shown) directly to the sample cartridge 506 for sampling of air provided through the air flow tube.

Additionally, in embodiments, the handle device 784 may be configured to be coupled to a container 752 that is configured to enclose the sample cartridge 506, thereby facilitating avoiding exposure of the sample cartridge 506 to contamination. For example, as shown in FIGS. 7D and 7E, embodiments include a cylindrical container 752 having internal threading 754 configured to mate with a second threading 756 disposed on an attachment portion 758 of the handle device 748. According to embodiments, the container 752 may be configured according to any number of different shapes and may be configured to be removably coupled to the handle device 748 using any number of different attachment mechanisms such as, for example, compression fittings, tabs, clips, and/or the like. In the illustrated embodiments, an attachment nut 760 is configured to be secured within the attachment portion 758 of the handle device 748. As shown, a first stem 762 of a storage mount stud 764 includes threading 766 that is configured to mate with internal threading 768 of the attachment nut 760. The first exterior portion 746 of the handle device 748 may be, or include, a second stem of the storage mount stud 764. In this manner, when the attachment nut 760 is disposed within the attachment portion 758 of the handle device 748 and the storage mount stud 764 is coupled thereto, the sample cartridge 506 may be screwed onto the handle device 748. The sample cartridge 506 may be inserted into an opening 770 of the container 750, which may be removably coupled to the handle device 748. According to embodiments, any number of other types of handle devices, coupling mechanisms, containers, and/or the like may be utilized for providing protection to the sample cartridge 506.

According to embodiments, a miniature thermophoretic sampler can be designed to be coupled upstream of an active sampling aerosol monitor to collect aerosol (e.g., nanoparticles, gases and other airborne particulate matter) for subsequent physical and chemical analyses. In embodiments, the sampler collects airborne nanoparticles onto a substrate while providing minimal interference with a downstream, active-sampling aerosol monitor so that, for example, a real-time continuous monitor may also capture a time-integrated sample for subsequent laboratory characterization and analysis. Analysis of samples collected by embodiments of the sampler may provide forensic information on the sampled aerosol (e.g., size distribution, shape, chemical and physical composition of particles). In embodiments, the thermophoretic sampler uses thermophoretic force to collect a small percentage (e.g., less than 5%) of the sampled aerosol onto a substrate, while the remainder of the sampled aerosol flows into an active monitor, gas monitor, biosensor, and/or the like.

FIG. 8A shows an illustrative thermophoretic sampler 800 that is configured for attachment to a device such as, for example, active sampling aerosol monitor, in accordance with embodiments of the disclosed subject matter. As shown, the sampler 800 includes a sample chamber housing 810 that includes a cartridge channel 812 configured to receive a sample cartridge 814. In embodiments, the cartridge channel 812 and sample cartridge 814 can be similar to the cartridge channel 52 and the sample cartridge 12 described above with reference, for example, to FIGS. 1A, 1C, 1D, and the cartridge channel 306 and cartridge 300 described above with reference to FIGS. 3A and 3B. In the illustrated embodiments, the sample chamber housing 810 includes a sample chamber 816 partially defined by a tube portion 818. In embodiments, an end 820 of the tube portion 818 can be adapted to be removably coupled to an inlet of an air intake device (not shown) that may be used, for example, to collect aerosol samples, analyze aerosol samples, and/or the like. According to embodiments, the sampler 800 can be used as an upstream nanoparticle sampler in conjunction with other types of particle collectors, samplers, and/or analyzers.

As shown in FIG. 8A, the tube portion 818 includes an aperture 822 through which a substrate 824 is exposed to the sample chamber 816. A cooling mechanism 826 can be thermally coupled to the substrate 824 to facilitate reducing the temperature of the substrate 824 below a temperature of a "warm" region 828 of the sample chamber 816. In embodiments, the cooling mechanism 826 can be similar to cooling mechanisms described herein with reference to other embodiments of the disclosed subject matter. In embodiments, a heating mechanism 830 can be disposed on an upper surface 832 of the tube portion 818 to facilitate introducing heat to the "warm" region 828.

FIGS. 8B and 8C are schematic diagrams depicting other embodiments of a sampler 834 in which a sample chamber 836 that is smaller than the tube portion 838 is defined by placement of a cooling mechanism 840 and a heating mechanism 842. For example, in embodiments, the cooling mechanism 840 can be disposed below the tube portion 838, and the heating mechanism 842 can be disposed a desired distance above the cooling mechanism 840, within the tube portion 838. In embodiments, the positions of the cooling mechanism 840 and/or the heating mechanism 842 can be adjustable.

FIG. 8D is a schematic diagram depicting embodiments of a thermophoretic sampler 850 that can be used in conjunction with other devices. As shown in FIG. 7B, the sampler 850 includes a tube portion 852 having an end 854 adapted for coupling to another device (not shown). In the illustrated embodiments, a sampling chamber 856 is provided in a secondary flow path 858. According to embodiments, a cooling mechanism 860 and/or a heating mechanism 862 can be used to induce thermophoresis within the sampling chamber 856. In embodiments, the secondary flow path 858 can be passive such that a portion of air flowing through the tube portion 852 is naturally diverted into the secondary flow path 858. In other embodiments, the secondary flow path 858 includes a pump 864 that pulls air into the secondary flow path 858.

FIG. 8E is a schematic diagram depicting an illustrative operating environment 868 in which a thermophoretic sampler 870 is coupled to an active sampling aerosol monitor 872, in accordance with embodiments of the disclosed subject matter. The illustrative operating environment 868 shown in FIG. 8E is not intended to suggest any limitation as to the scope of use or functionality of embodiments of the subject matter disclosed throughout this document. Neither should the illustrative operating environment 868 be interpreted as having any dependency or requirement related to any single component or combination of components illustrated therein. For example, in embodiments, the illustrative operating environment 868 can include additional components such as, for example components of an active particle monitor 872, activity sensors (e.g., accelerometers), and/or the like. Additionally, any one or more of the components depicted in FIG. 8E can be, in embodiments, integrated with various ones of the other components depicted therein (and/or components not illustrated).

According to embodiments, the active sampling aerosol monitor 872 may be, or include, monitors such as, for example, a direct reading instrument (DRI) 874, a gas detector 876, a biosensor 878, and/or the like. In embodiments, a monitor 872 (or component thereof) may be used to trigger (e.g., via communication with a controller 880) or control the thermophoretic sampler 870. In embodiments, the position of the substrate (not shown) can be controlled using a mechanical positioner 882, which may be triggered and/or controlled by either the thermophoretic sampler 870 or one or more monitors. For example, in embodiments, a DRI 874 may trigger the thermophoretic sampler 870 to begin collecting nanoparticles onto an appropriate substrate in response to sensing a spike in nanoparticle concentration level. As another example, in embodiments, a gas detector 876 may trigger the thermophoretic sampler 870 to begin collecting nanoparticles onto an appropriate substrate in response to sensing a specific gas concentration level. As another example, in embodiments, biosensor 878 may trigger the thermophoretic sampler to begin collecting nanoparticles onto an appropriate substrate in response to detecting a specific biogen concentration level.

Figure 9:
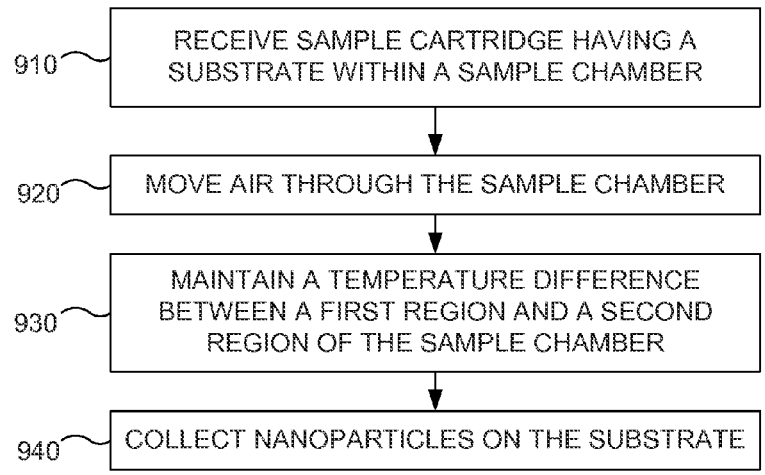
FIG. 9 is a flow diagram depicting an illustrative method of collecting nanoparticles in accordance with embodiments of the disclosure.

FIG. 9 is a flow diagram depicting an illustrative method for collecting nanoparticles in accordance with embodiments of the disclosed subject matter. According to embodiments of the illustrative method, a sample chamber receives a sample cartridge having a substrate disposed thereon (block 910). Air is moved through the sample chamber (block 920) and a controller is used to maintain a temperature difference between a first region and a second region of the sample chamber, thereby inducing thermophoresis (block 930). Due to the thermophoresis, nanoparticles are collected on the substrate (block 940).

Figure 10:
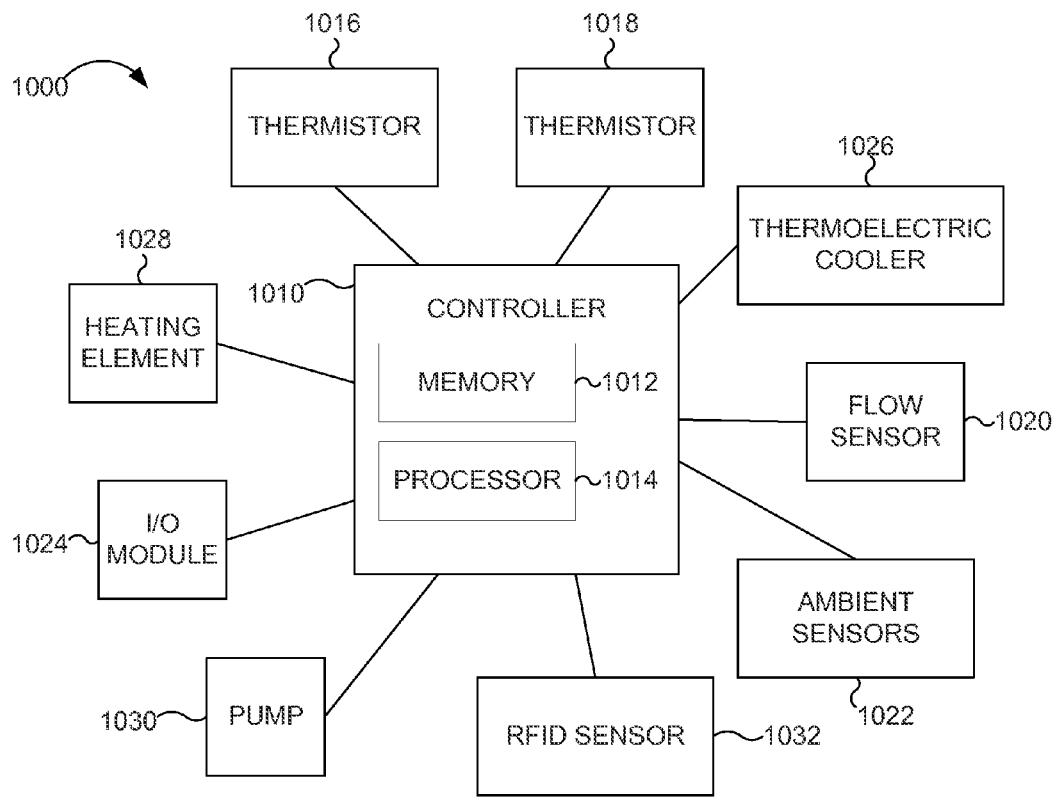
FIG. 10 is a block diagram illustrating an operating environment in accordance with embodiments of the disclosure.

FIG. 10 depicts an illustrative operating environment 1000 associated with a personal thermophoretic sampler, aspects of embodiments of which are depicted, for example, in FIGS. 1A-9. The illustrative operating environment 1000 includes a controller 1010 that facilitates various aspects of operations described herein. For example, in embodiments, the controller 1010 can maintain a temperature difference between the substrate and a "warm" region of the sample chamber, control the pump, and/or the like. According to embodiments, the controller can include a one or more memory components 1012 and one or more processors 1014. In embodiments, the controller 1010 can receive information from a number of different sources, can store information in the memory component 1012 and can use the processor(s) 1014, for example, to execute computer-executable instructions (which may be stored in the memory component 1012) that cause the controller to perform any number of different processes, methods, actions, and/or the like. For example, in embodiments, the controller 1010 receives temperature measurements from one or more thermistors 1016 and 1018, air flow measurements from a flow sensor 1020, measurements of ambient conditions (e.g., ambient temperature, ambient air pressure, ambient relative humidity) from ambient sensors 1022, input from a user via an input/output (I/O) module 1024, and/or the like, and can use some or all of the received information to perform algorithms that facilitate aspects of functionality described herein.

In embodiments, the controller 1010 creates a thermophoretic temperature differential between two regions of a sample chamber using a thermoelectric cooler 1026 and, in embodiments, a heating element 1028 (e.g., a resistive heater). In embodiments, for example, heat flow can be regulated using proportional-integral-differential (PID) control software that feeds back into the thermoelectric cooler 1026 and heating element 1028. Air flow can be monitored using flow measurements received from the flow sensor 1020 and can be controlled using a pump 1030. According to embodiments, the controller 1010 can utilize any number of different control algorithms, servos, hardware, firmware, and/or the like, to maintain temperature differentials, time sampling procedures, regulate air flow, and/or the like. In embodiments, for example, a programmable logic device can be used as a safety shut-off in case of temperature fault.

Additionally, as depicted in FIG. 10, the controller 1010 can communicate with a radio frequency identification (RFID) sensor 1032 or other communication module. In embodiments, other types of communication modules can be used such as, for example, wireless communication modules, wired communication modules, and/or the like. For example, in embodiments, the RFID sensor 1032 can receive information from an RFID tag associated with a sample cartridge. In embodiments, the RFID tag can include information identifying a user, information identifying a particular sampling procedure to be followed, and/or the like. In embodiments, the RFID sensor 1032 can be configured to receive information from an RFID tag attached by a person, disposed in a doorframe, located at a workstation, and/or the like, such that the controller 1010 can obtain information associated with a particular environment, user, and/or the like.

The illustrative operating environment 1000 shown in FIG. 10 is not intended to suggest any limitation as to the scope of use or functionality of embodiments of the subject matter disclosed throughout this document. Neither should the illustrative operating environment 1000 be interpreted as having any dependency or requirement related to any single component or combination of components illustrated therein. For example, in embodiments, the illustrative operating environment 1000 can include additional components such as, for example components of an active particle monitor, activity sensors (e.g., accelerometers), and/or the like. Additionally, any one or more of the components depicted in FIG. 10 can be, in embodiments, integrated with various ones of the other components depicted therein (and/or components not illustrated). Any number of other components or combinations of components can be integrated with the illustrative operating environment 1000 depicted in FIG. 10, all of which are considered to be within the scope of this disclosure.

Embodiments of the disclosed subject matter are described in the general context of computer-executable instructions. Computer-executable instructions can include, for example, computer code, machine-usable instructions, and/or the like such as, for example, program components, capable of being executed by one or more processors associated with a computing device. Generally, program components including routines, programs, objects, modules, data structures, portions of one or more of the preceding, and/or the like, refer to code that, when executed, causes a computing device (e.g., a processor) to perform particular tasks (e.g., methods, calculations, etc.) or implement or manipulate various abstract data types. Some or all of the functionality contemplated herein can also be implemented in hardware, software, or a combination of software, hardware, and/or firmware.

In embodiments, the memory component 1012 can include computer-readable media. Computer-readable media include both volatile and non-volatile media, removable and nonremovable media, and contemplate media readable by a database, a processor, a router, and various other networked devices. By way of example, and not limitation, computer-readable media can include media implemented in any method or technology for storing information. Examples of stored information include computer-executable instructions, data structures, program modules, and other data representations. Media examples include, but are not limited to, Random Access Memory (RAM); Read Only Memory (ROM); Electronically Erasable Programmable Read Only Memory (EEPROM); flash memory or other memory technologies; Compact Disc Read-Only Memory (CD-ROM), digital versatile disks (DVDs) or other optical or holographic media; magnetic cassettes, magnetic tape, magnetic disk storage or other magnetic storage devices; data transmissions; or any other medium that can be used to encode information and can be accessed by a computing device such as, for example, quantum state memory, and/or the like.

According to embodiments, various components of the operating environment 1000 can be implemented on one or more computing devices that are communicatively coupled to the thermophoretic sampler. According to embodiments, the computing device can include any type of computing device suitable for implementing embodiments of the disclosed subject matter. Examples of computing devices include "processors," "controllers," "workstations," "servers," "laptops," "desktops," "tablet computers," "hand-held devices," and/or the like, all of which are contemplated within the scope of FIG. 10 and reference to various components of the operating environment 1000. In embodiments, components of the operating environment 1000 can include more than one computing device such as, for example, in a distributing computing environment, a networked environment, and/or the like. For example, in embodiments, portions of the components of the operating environment 1000 can be hosted on a computing device in a sampler, while other portions can be hosted on a handheld device, laptop, or other computing device.

In embodiments, a computing device includes a bus that, directly and/or indirectly, couples the following devices: a processor, a memory, an input/output (I/O) port, an I/O component, and a power supply. Any number of additional components, different components, and/or combinations of components can also be included in the computing device. The bus represents what may be one or more busses (such as, for example, an address bus, data bus, or combination thereof). Similarly, in embodiments, the computing device can include a number of processors, a number of memory components, a number of I/O ports, a number of I/O components, and/or a number of power supplies. According to embodiments, the processor (or processors) reads data from various entities such as a memory component, user interface, or sensors.

While the subject matter of embodiments of the disclosure is described with specificity, the description itself is not intended to limit the scope of this patent. Rather, the inventors have contemplated that the claimed subject matter might also be embodied in other ways, to include different steps or features, or combinations of steps or features similar to the ones described in this document, in conjunction with other technologies. For example, in embodiments, a number of substrates can be coupled to a movable (e.g., slidable, rotatable, and/or the like) substrate holder that moves each substrate into a position in which it is exposed to the sample chamber in succession, thereby facilitating nanoparticle collection in a controllable time series. Additionally, in embodiments, for example, a thermophoretic sampler may include an impactor that can be used to limit the size of particles entering the sample chamber. Furthermore, in various embodiments, any number of different features and/or components described above may be designed according to any number of different shapes, and may include any number of different contours, corners, curves, and/or other design features that may be adapted for aesthetic and/or functional purposes.

The following is claimed:

1. A thermophoretic sampling device, the device comprising:
   a sample chamber housing, comprising:
      an upper chamber boundary defined within the sample chamber housing; and
      a cartridge channel defined within the sample chamber housing; and
   a sample cartridge configured to be removably inserted into the cartridge channel, the sample cartridge comprising:
      an upper surface, wherein a notch is defined in the upper surface, the notch corresponding to the upper chamber boundary such that, when the sample cartridge is inserted into the cartridge channel, a sample chamber is provided, the sample chamber defining a portion of a flow path for air;
      a substrate, coupled to a first portion of the sample cartridge, the substrate having a collection surface configured to be exposed to a first region of the sample chamber in response to the sample cartridge being inserted into the cartridge channel;
      an air inlet defined in a first end of a second portion of the sample cartridge; and
      an inlet duct extending from the air inlet to an aperture defined in a second end of the second portion of the sample cartridge, wherein the inlet duct is configured to allow air to move from the air inlet to the sample chamber.

2. The device of claim 1, the notch comprising a space at least partially defined by a lower internal surface, a first internal side surface, and a second internal side surface, the sample cartridge further comprising:
   a bottom surface; and
   a depression at least partially defined in the lower internal surface, the depression extending at least partially in a direction toward the sample chamber and away from the aperture defined in the second end of the second portion of the sample cartridge.

3. The device of claim 1, wherein the sample cartridge further comprises threading disposed on an internal surface of the inlet duct.

4. The device of claim 3, wherein the threading is configured to facilitate connection of a handle device with the sample cartridge.

5. The device of claim 1, wherein the sample chamber housing includes a thermoelectric cooler.

6. The device of claim 5, wherein the sample cartridge further comprises a first thermal conduction element that is thermally coupled to the substrate, where the first thermal conduction element is configured to be thermally coupled to the thermoelectric cooler in response to the sample cartridge being inserted into the cartridge channel.

7. The device of claim 6, wherein the thermoelectric cooler comprises a first surface and a second surface, wherein the first surface of the thermoelectric cooler is configured to contact a first surface of the first thermal conduction element and, wherein the second surface of the thermoelectric cooler contacts a heat dispersion mechanism.

8. The device of claim 7, the heat dispersion mechanism comprising at least one of a thermally conductive housing and a heat sink.

9. The device of claim 6, further comprising:
a second thermal conduction element having a first surface and a second surface, wherein the first surface of the second thermal conduction element is exposed to a second region of the sample chamber; and
a heating element having a surface that contacts the second surface of the second thermal conduction element.

10. The device of claim 6, the first portion of the cartridge comprising:
a bottom surface, wherein a first opening is defined in the bottom surface;
an upper surface, wherein a notch is defined in the upper surface;
a second opening, wherein the second opening is defined in an inside surface of the notch; and
a hollow channel extending from the first opening to the second opening, wherein the first thermal conduction element is disposed within the hollow channel such that the surface of the first thermal conduction element extends from the first opening.

11. The device of claim 6, wherein the surface of the first thermal conduction element includes an angled feature that facilitates application of an upward force on the surface when the first portion of the cartridge is inserted into the cartridge channel, and wherein the upward force causes compression of an elastic mechanism disposed within the hollow channel, thereby facilitating thermal coupling between the substrate and the first thermal conduction element.

12. The device of claim 1, wherein the sample cartridge further comprises threading disposed on an internal surface of the inlet duct, wherein the threading is configured to facilitate connection of a handle device with the sample cartridge.

13. A system for collecting nanoparticles on a substrate, the system comprising:
a sample core assembly having a sample chamber defined therein, the sample core assembly comprising:
an opening defined in an outside wall of the sample core assembly;
a cooling mechanism; and
a cartridge channel extending from the opening to the sample chamber;
a sample cartridge configured to be removably inserted into the cartridge channel through the opening, the sample cartridge comprising:
a first portion configured to be disposed within the cartridge channel;
a second portion adjacent to the first portion;
an air inlet disposed in a first end of the second portion; and
an inlet duct disposed within the second portion, the inlet duct extending from the air inlet to an aperture defined in a second end of the second portion; and
a substrate removably coupled to the sample cartridge, wherein the cooling mechanism is configured to be thermally coupled to the substrate in response to the sample cartridge being inserted into the cartridge channel.

14. The system of claim 13, further comprising a controller that controls the cooling mechanism to maintain the substrate at a temperature that is lower than a temperature of a warm region of the sample chamber, thereby inducing thermophoresis.

15. The system of claim 13, further comprising a heating element that applies heat to the warm region of the sample chamber.

16. The system of claim 13, further comprising an air flow mechanism, the air flow mechanism comprising:
a pump that pulls air into the sample core assembly through the air inlet; and
a flow sensor that determines an amount of air being moved through the sample core assembly.

17. The system of claim 13, wherein the sample cartridge comprises a radio-frequency identification (RFID) tag and, wherein the sample core assembly comprises an RFID sensor that obtains information from the RFID tag.

18. The system of claim 13, further comprising an ambient sensor that measures at least one of an ambient temperature, an ambient air pressure, and an ambient relative humidity.

19. The system of claim 13, the sample cartridge further comprising:
a bottom surface;
an upper surface, wherein a notch is defined in the upper surface, the notch comprising a space at least partially defined by a lower internal surface, a first internal side surface, and a second internal side surface; and
a depression at least partially defined in the lower internal surface, the depression extending, at least partially in a direction toward the sample chamber and away from the aperture defined in the second end of the second portion.

20. A method for collecting nanoparticles on a substrate, the method comprising:
receiving a sample cartridge, having a substrate removably coupled thereto, within a sample core assembly, the sample core assembly comprising a cartridge channel configured to receive a first portion of the sample cartridge, and an upper chamber boundary; wherein the sample cartridge comprises an air inlet defined in a first end, an inlet duct extending from the air inlet to the sample chamber, and an upper surface, wherein a notch is defined in the upper surface, the notch corresponding to the upper chamber boundary such that, when the sample cartridge is received into the cartridge channel, a sample chamber is provided, the sample chamber defining a portion of a flow path for air; and
maintaining the substrate at a temperature that is lower than a temperature of a warm region of the sample chamber such that thermophoresis causes nanoparticles to be deposited on the substrate.

* * * * *